US012629363B2

(12) United States Patent
Lesage et al.

(10) Patent No.: US 12,629,363 B2
(45) Date of Patent: May 19, 2026

(54) PROPHYLAXIS AND TREATMENT OF ANGIOEDEMA

(71) Applicant: PHARVARIS GMBH, Zug (CH)

(72) Inventors: Anne Lesage, Zug (CH); Peng Lu, Zug (CH)

(73) Assignee: Pharvaris GmbH, Zug (CH)

( * ) Notice: Subject to any disclaimer, the term of this patent is extended or adjusted under 35 U.S.C. 154(b) by 425 days.

(21) Appl. No.: 18/036,719

(22) PCT Filed: Nov. 12, 2021

(86) PCT No.: PCT/EP2021/081493

§ 371 (c)(1),
(2) Date: May 12, 2023

(87) PCT Pub. No.: WO2022/101395

PCT Pub. Date: May 19, 2022

(65) Prior Publication Data

US 2023/0338358 A1 Oct. 26, 2023

(30) Foreign Application Priority Data

Nov. 12, 2020 (EP) .................................... 20207273

(51) Int. Cl.
*A61K 31/4709* (2006.01)
*A61K 9/00* (2006.01)
(Continued)

(52) U.S. Cl.
CPC ........ *A61K 31/4709* (2013.01); *A61K 9/0053* (2013.01); *A61K 31/496* (2013.01); *A61P 7/10* (2018.01)

(58) Field of Classification Search
CPC ............................. A61K 31/4709; A61P 7/10
(Continued)

(56) References Cited

U.S. PATENT DOCUMENTS

| | | | | |
|---|---|---|---|---|
| 10,836,748 B2 * | 11/2020 | Gibson | ............... | C07D 401/14 |
| 11,820,756 B2 * | 11/2023 | Gibson | ............... | C07D 401/14 |
| 12,312,330 B2 | 5/2025 | Gibson et al. | | |
| 12,391,681 B2 | 8/2025 | Gibson et al. | | |
| 2008/0249076 A1 | 10/2008 | Holm et al. | | |
| 2016/0030416 A1 | 2/2016 | Leach et al. | | |

FOREIGN PATENT DOCUMENTS

| | | |
|---|---|---|
| JP | 2016-514141 A | 5/2016 |
| JP | 2017-145262 A | 8/2017 |

(Continued)

OTHER PUBLICATIONS

Jill Seladi-Schulman, What Are Antifungal Drugs?, Healthline, Dec. 6, 2019, p. 1-10. (Year: 2019).*

(Continued)

*Primary Examiner* — Jeffrey S Lundgren
*Assistant Examiner* — Heather Dahlin
(74) *Attorney, Agent, or Firm* — Clark & Elbing LLP

(57) ABSTRACT

The invention relates to a bradykinin (BK) B2-receptor antagonist having structural formula (I) for use in prophylactic treatment of angioedema (AE) or in a method of treating AE, wherein said compound is at least once orally administered in a therapeutically effective dose to prevent, alleviate or treat AE symptoms. This invention also provides a method of prophylactic treatment of a human patient suffering from AE or a method for on-demand treatment of a human patient who has experienced an acute AE attack, comprising orally administering to the human patient a therapeutically effective dose of the compound of formula (Continued)

(I) at least once to thereby alleviate or treat AE symptoms of the patient.

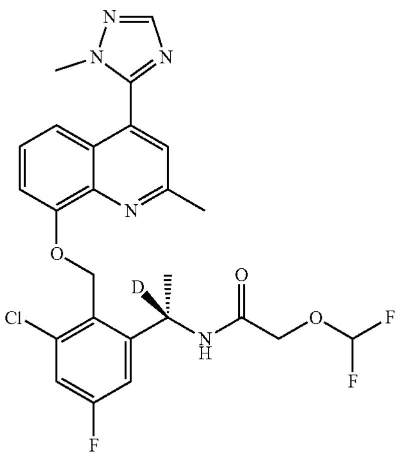

(I)

17 Claims, 8 Drawing Sheets

(51) Int. Cl.
*A61K 31/496* (2006.01)
*A61P 7/10* (2006.01)

(58) Field of Classification Search
USPC .......................................................... 514/314
See application file for complete search history.

(56) References Cited

FOREIGN PATENT DOCUMENTS

| | | | | |
|---|---|---|---|---|
| WO | WO-2008/116620 A1 | 10/2008 | | |
| WO | WO-2010/031589 A1 | 3/2010 | | |
| WO | WO-2011/069094 A1 | 6/2011 | | |
| WO | WO-2014/159637 A1 | 10/2014 | | |
| WO | WO 2019101906 A1 * | 5/2019 | ........... | C07D 401/14 |

OTHER PUBLICATIONS

Sweet, Lawrence C.; Jackson, Charles E.; Yanari, Sam S.; and Yott, J. B. (1980) "Danazol Therapy in Hereditary Angioedema," Henry Ford Hospital Medical Journal : vol. 28 : No. 1 , 31-36. (Year: 1980).*

Konishi H, Takenaka A, Minouchi T, Yamaji A. Impairment of CYP3A4 capacity in patients receiving danazol therapy: examination on oxidative cortisol metabolism. Hormone and Metabolic Research. Oct. 2001;33(10):628-30. (Year: 2001).*

Lesage et al., "In Vitro Pharmacological Profile of a New Small Molecule Bradykinin B2 Receptor Antagonist," Front Pharmacol. 11:916 (Jun. 2020) (16 pages).

Sachiko, BE., "Diagnosis and Treatment of Hereditary Angioedema," Bulletin of the Japanese Society of Otolaryngology. 122(11):1457-1459 (2019) (5 pages).

Gibson et al., "Novel small molecule bradykinin B2 receptor antagonists," J Med Chem. 52(14):4370-9 (Jul. 2009).

Mitsubishi Tanabe Pharma Corporation, Bonzol Tablet 200 mg Pharmaceutical Interview Form, 9th edition. Revised Oct. 2012 (67 pages).

Nozaki et al., Medicinal Chemistry. Kagaku-Dojin Publishing Company, INC., 98-99 (1995).

Wermuth, Chapter 13: Molecular Conversion based on Isosteric Substitution. The Practice of Medicinal Chemistry. vol 1. Technomics, Inc. 235-271 (1998) (38 pages).

* cited by examiner

PROPHYLAXIS AND TREATMENT OF ANGIOEDEMA

FIELD OF THE INVENTION

The invention relates to a bradykinin (BK) B2-receptor antagonist having structural formula (I) for use in prophylactic treatment of angioedema (AE) or in a method of treating AE, wherein said compound is at least once orally administered in a therapeutically effective dose to prevent, alleviate or treat AE symptoms. This invention also provides a method of prophylactic treatment of a human patient suffering from AE or a method for on-demand treatment of a human patient who has experienced an acute AE attack, comprising orally administering to the human patient a therapeutically effective dose of at least 0.1 mg of the compound of formula (I) at least once to thereby alleviate or treat AE symptoms of the patient.

BACKGROUND OF THE INVENTION

Angioedema (AE) is an area of swelling of the lower layer of skin and tissue just under the skin or mucous membranes. The debilitating and often painful swelling may occur in the face, lips, tongue, limbs, genitals, gastrointestinal mucosa, urogenital region and airways. Often it is associated with hives, which are swelling within the upper skin. It is characterized by repetitive episodes of swelling, and onset is typically over minutes to hours. Predicting where and when the next episode of angioedema will occur is impossible. Patients may have one episode per month, but there are also patients who have weekly episodes or only one or two episodes per year. Known forms of AE include hereditary angioedema (HAE), acquired angioedema (AAE), bradykinin-mediated non-histaminergic idiopathic angioedema, allergic angioedema, and drug induced angioedema.

HAE is a rare and potentially life-threatening genetic condition. HAE is an autosomal dominant disease, meaning that a defect in only one copy of the gene leads to symptoms and that it occurs at similar rates in both males and females. It is mainly caused by one or more mutations (inherited or spontaneous) in the SERPING 1 gene, which codes for the C1-esterase inhibitor protein C1-INH. Deficiency or malfunction of C1-INH leads to uncontrolled synthesis and activity of plasma kallikrein and unconstrained BK production. Excessive BK production is recognized to be the key mediator of symptoms in patients with HAE and manifests as edema attacks, most commonly in the limbs, face, throat, lips, tongue, intestinal tract, urogenital region and airways. HAE patients with a deficiency in C1-INH activity are classified as Type 1 or Type 2. Type I is the most common form and results in low levels of circulating C1-INH, and Type 2 results in production of a low function protein. An additional form of HAE, called normal C1-INH HAE, can occur in patients with normal levels of C1-INH for a variety of reasons including mutations in genes for Factor XII, plasminogen, angiopoietin-1 or kininogen-1. Moreover, bradykinin-induced acute attacks of angioedema can occur idiopathically in individuals for which a hereditary cause has not yet been identified. Excessive amounts of BK can also be caused by increased circulation of estrogens, reduced C1-INH levels due to underlying diseases, reduced elimination of BK, or through use of medications such as angiotensin-converting enzyme (ACE) inhibitors and tissue plasminogen activator (tPA).

Excessive BK generation and increased risks for edema attacks in HAE may occur during conditions associated with inflammation, infections, ischemia and allergic reactions. Attacks often lead to discomfort, pain and nausea but can become life threatening in the case of airway obstruction, with a 30% risk of asphyxiation if the attack remains untreated. The number and severity of attacks vary highly between patients, and the most severely affected patients can experience attacks every few days. Attacks can occur spontaneously although they often are associated with anxiety, stress, minor trauma, surgery, or illnesses. Commonly patients are alerted to an impending attack by prodromal symptoms which include rash, fatigue, and muscle aches. The severity of attacks is unpredictable and not related to their underlying frequency. Airway swelling, e.g. swelling affecting the throat or larynx, is particularly dangerous and may lead to death due to asphyxiation. Although rare, at least half of HAE patients have experienced a life-threatening airway swelling attack and airway attacks remain a major cause of mortality in HAE patients. Swelling typically develops over 0-36 hours and resolves in 3-5 days without treatment. Symptoms typically present in young children and may take 5-10 years or until early adolescence or young adulthood to be diagnosed. Global prevalence of individuals affected with HAE ranges from 1:10,000 to 1:150,000, or at least 6,600 patients in the U.S. and at least 8,900 patients in the EU.

There are currently two treatment approaches to the management of AE: acute (on-demand) treatment of attacks and prevention of attacks with short or long-term prophylactic therapy.

At this time, all approved products for treatment of HAE have to be administered parenterally. These products include C1-INH replacement products such as human plasma-derived C1-INH concentrates (Berinert®, Cinryze®), which must be stored at 2° C. to 25° C. (36° F. to 77° F.), CetorR or recombinant human C1-INH (Ruconest®), the B2 receptor antagonist icatibant (Firazyr®), and the plasma kallikrein inhibitor ecallantide (Kalbitor®), which has been known to cause allergic reactions including anaphylaxis and must be administered by a doctor or nurse in a healthcare setting. Icatibant, which must be administered by subcutaneous injection by a healthcare professional, is the only available B2 receptor antagonist indicated for treatment of acute HAE attacks Type 1 or Type 2 with C1-INH deficiency. In acute HAE attacks, icatibant has been shown to provide a significantly faster onset of relief than placebo (2.0 h versus 19.8 h) (Lumry et al., Ann Allergy Asthma Immunol. (107), 529-537, 2011). Icatibant is recommended as a first-line treatment option for the treatment of acute HAE attacks in patients with HAE (Maurer et al., Allergy. (00), 1-22, 2018; DOI: 10.1111/all.13384).

The currently approved prophylactic therapies for HAE include the C1-INH replacement products such as intravenously administered Cinryze®; subcutaneously administered Haegarda®//Berinert®2000/3000, which requires twice weekly injections; and the monoclonal antibody and plasma kallikrein inhibitor lanadelumab-flyo (sc Takhzyro®). Current treatment guidelines recommend against the use of the traditional oral medications for HAE, such as antifibrinolytics (tranexamic acid or epsilon aminocaproic acid), due to their limited efficacy (Stoppa-Lyonnet et al., N Engl J Med (317), 1-6, 1987; DOI: 10.1056/NEJM198707023170101). Attenuated androgens, e.g. danazol, stanozolol, and oxandrolone, are only recommended as second line treatments for the prevention of HAE attacks, since there are numerous contraindications, therapeutic class adverse events and overall suboptimal control of HAE in many patients. The use of attenuated androgens is limited by numerous safety issues, including seborrhea, altered libido, depression, fatigue, menstrual abnormalities, and masculinization.

All in all, presently available therapies of AE are associated with numerous drawbacks. Most of the currently recommended medicaments need to be administered by injection, which patients regularly find challenging because they often suffer from painful injection-site reactions leading some patients to delay treatment and risk attacks. In general, administration by injection is inconvenient as taking the medicament is more complicated and time consuming (some medicaments need to be administered in a clinic); and some injectable medicaments moreover require particular storage conditions. Further, irrespective of their efficacy, many known therapies are associated with severe side effects or hampered by numerous contraindications.

In view of the deficits of the currently available therapies to treat AE, there is a need for an oral therapy for on-demand (acute) and prophylctic treatment of AE. In partiuclar, there is a need for a compound that can be used in a method of prophylactic treatment of a human patient suffering from HAE or on-demand treatment of a human patient who has experienced an acute HAE attack, and that can be orally administered to the human patient in need thereof in a therapeutically effective dose to prevent, alleviate or treat HAE symptoms.

These objects are solved by the subject matter of the attached claims as will become apparent upon reference to the following description and definitions.

SUMMARY OF THE INVENTION

The present invention was made in view of the prior art and the needs described above, and, therefore, the present invention provides a compound having the structural formula (I) for use in prophylactic treatment of angioedema (AE) or in a method of treating AE, wherein said compound is at least once orally administered in a therapeutically effective dose to prevent, treat or alleviate AE symptoms.

The present invention further provides the compound of formula (I) for use in the prophylactic treatment of angioedema (AE) or in a method of treating AE as mentioned above, wherein said use further comprises administering at least one additional therapeutic agent such as a CYP34A inhibitor.

This invention also provides a method of prophylactic treatment of a human patient suffering from AE or a method for on-demand treatment of a human patient who has experienced an acute AE attack, comprising orally administering to the human patient in need thereof at least once a therapeutically effective dose of the compound of formula (I) to thereby prevent, alleviate or treat AE symptoms of the patient. This method of prophylactic or on-demand treatment may further comprise administering to the patient at least one additional therapeutic agent such as a CYP34A inhibitor.

DESCRIPTION OF THE INVENTION

Figure 1:
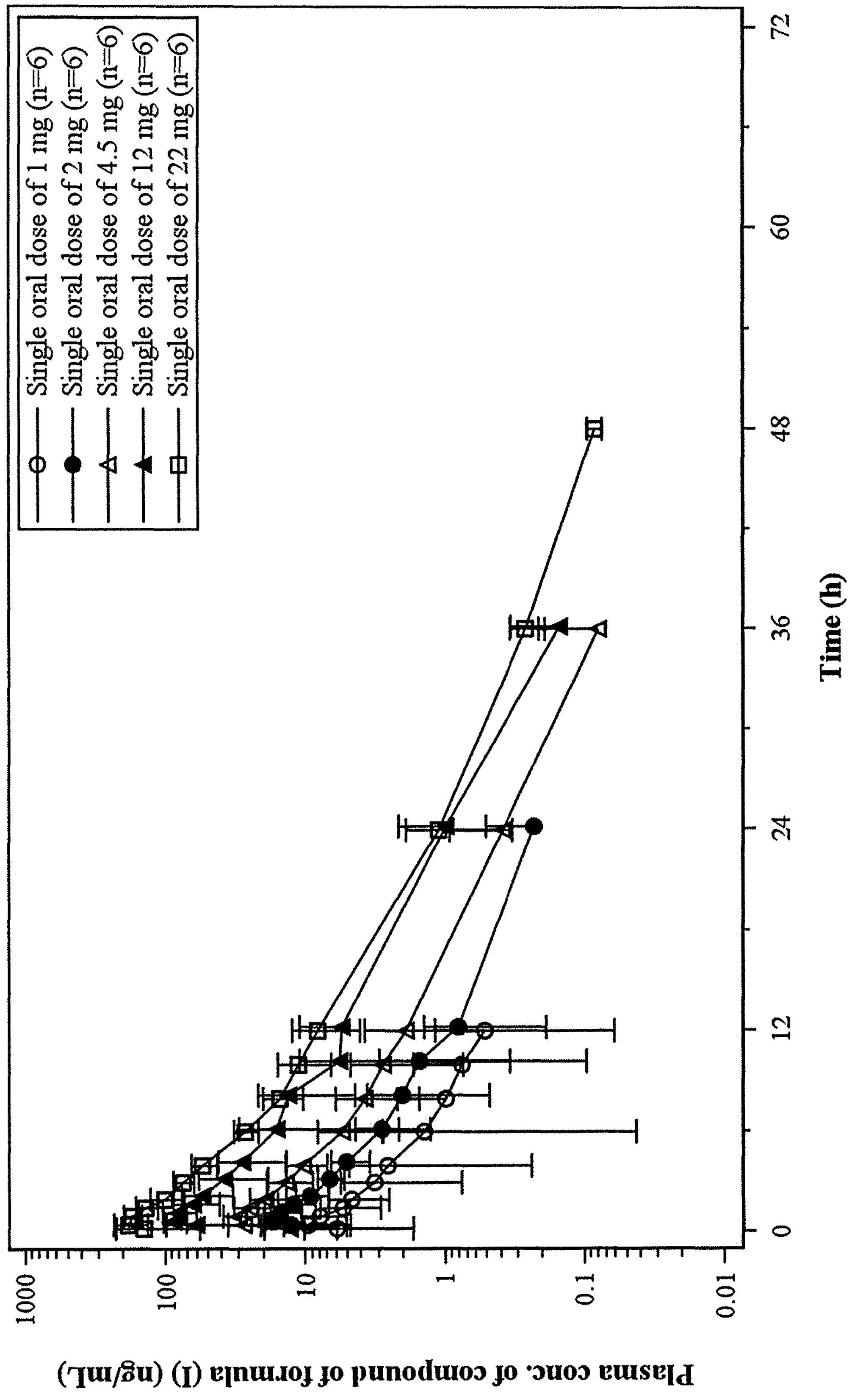
FIG. 1. Plasma levels of the compound of formula (I) observed in healthy volunteers under fasted conditions after oral administration of a single dose of from 1 to 22 mg of the compound. Graphs display mean including standard deviation bars.

The present invention provides a compound having the structural formula (I):

(I)

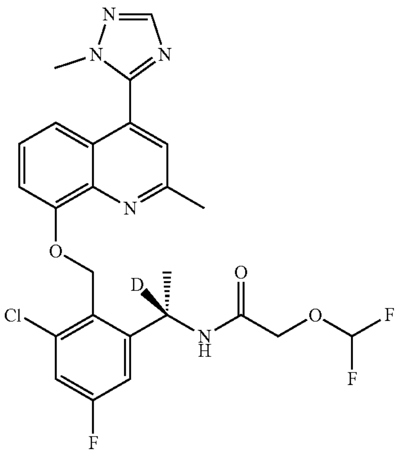

for use in prophylactic treatment of angioedema (AE) or in a method of treating AE, wherein said compound is at least once orally administered in a therapeutically effective dose to prevent, alleviate or treat AE symptoms. The present inventions also provides methods using the compound of formula (I) in the prophylactic or on-demand treatment of AE. Preferably, the AE is a bradykinin-mediated angioedema.

According to the present invention, a dose can be administered as a single dose or in a plurality of doses.

As used herein, the term "patient" or "subject" encompasses mammals. A patient, as used herein is a mammal that has at least one symptom of a condition described herein (e.g. angioedema (AE)). In one aspect, the mammal is a human.

As used herein, the term "treatment" encompasses both disease-modifying treatment and symptomatic treatment, either of which may be prophylactic (i.e., before the onset of symptoms, in order to prevent, delay or reduce the severity of symptoms) or therapeutic (i.e., after the onset of symptoms, in order to alleviate, abate or reduce the severity and/or duration of at least one of the symptoms and/or prevent additional symptoms). Therapeutic treatment can, for example, be "acute treatment" or "on-demand treatment", where it is imperative to immediately halt the progression of the edema and alleviate the symptoms. This applies particularly to AE symptoms or episodes (acute AE attack(s)) affecting the larynx, which can cause death by suffocation if left untreated.

As used herein, the term "therapeutically effective amount or dose" means an amount of the compound of formula (I) that produces a result that in and of itself helps to heal, cure, alleviate, abate or reduce the severity and/or duration of at least one symptom associated with AE.

In prophylactic uses (i.e. "prohylaxis"), the compound of formula (I) is administered to a subject or patient susceptible to or otherwise at risk of a particular condition. Such an amount is defined to be a "prophylactically effective amount or dose." Prophylactic treatments include administering to a patient who previously experienced at least one symptom of AE and is currently in remission, the compound of formula (I) in order to prevent a return of symptoms of AE.

As used herein, "short-term prophylactic treatment" or "short-term prohylaxis" refers to administration of the compound of formula (I) for a period of time before, and optionally after, exposure to trigger(s) that are likely to cause AE symptoms or AE attack(s), such as event(s) or procedure(s) including, but not limited to, anxiety, stress, minor trauma, surgery, medical or dental procedures and illnesses. In some instances, "short-term prohylaxis" includes the administration of at least one dose of the compound of formula (I) at least 30 minutes, at least 1 hour, at least 2 hours or at least 1 day prior to exposure to a trigger. Depending upon the severity and duration of the trigger, one or more additional doses may be administered after exposure to the trigger. An option for short-term prophylaxis is to administer at least one dose of the compound of formula (I) for at least five days prior to exposure to a trigger, and to administer at least one further dose of the compound of formula (I) at least one, at least two days, at least three days or at last four days after exposure to the trigger.

In certain embodiments wherein the condition of the patient or subject does not improve, the compound of formula (I) is administered chronically, that is, for an extended period of time, including throughout the duration of the life of the patient or subject in order to ameliorate or otherwise control or limit symptoms associated with AE in a the patient or subject.

In certain embodiments wherein status of a patient or subject does improve, the dose of drug being administered may be temporarily reduced or the interval between doses is extended or temporarily suspended for a certain length of time (i.e., a "drug holiday"). For instance, the interval between doses or the length of a drug holiday can be between 2 days and 1 year, including by way of example only, 2 days, 3 days, 4 days, 5 days, 6 days, 7 days, 10 days, 12 days, 15 days, 20 days, 28 days, 30 days or more than 30 days, a month, 2 months, 3 months, or 6 months. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

As used herein, "comprising", "including", "containing", "characterized by", and grammatical equivalents thereof are inclusive or open-ended terms that do not exclude additional, unrecited elements or method steps. Yet, "Comprising", etc. is also to be interpreted as including the more restrictive terms "consisting essentially of" and "consisting of", respectively.

As used herein, "consisting of" excludes any element, step, or ingredient not specified in the claim.

As used herein, the term "unit dosage" refers to physically discrete units suited as single administration dose for a subject to be treated, containing a therapeutically effective quantity of active compound in association with the required pharmaceutical carrier, e.g., a solution in a vial. The unit dosage can optionally comprise at least one, i.e. one or more, carrier substance, excipient and/or adjuvant.

In general, unless defined otherwise, technical and scientific terms used herein have the same meaning as commonly understood by one of ordinary skill in the art to which this invention belongs, and are consistent with general textbooks and dictionaries.

In accordance with the invention, there is provided:

[1] a compound having the following structural formula (I):

(I)

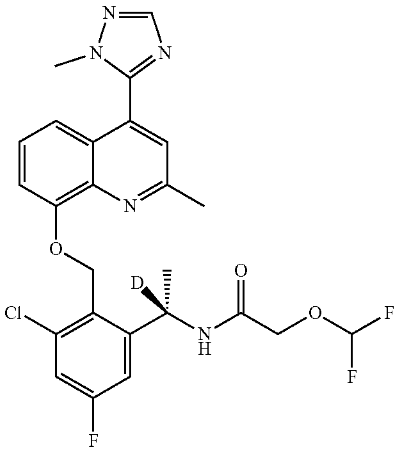

or a pharmaceutically acceptable salt, or solvate thereof, for use in prophylactic treatment of angioedema (AE) or in a method of treating AE, wherein said compound or a pharmaceutically acceptable salt, or solvate thereof, is orally administered at least once in a dose of up to 100 mg, preferably in a dose of up to 80 mg, 75 mg, 60 mg, 50 mg or 40 mg;

[2] the compound, or a pharmaceutically acceptable salt, or solvate thereof, for use according to [1], wherein the angioedema is hereditary angioedema (HAE), acquired angioedema (AAE), non-histaminergic idiopathic angioedema, allergic angioedema, drug-induced angioedema, or angioedema of unidentified cause; preferably the angioedema is bradykinin-mediated; more preferably the angioedema is bradykinin-mediated hereditary angioedema (HAE), bradykinin-mediated acquired angioedema (AAE), bradykinin-mediated non-histaminergic idiopathic angioedema, bradykinin-mediated allergic angioedema, bradykinin-mediated drug-induced angioedema or bradykinin-mediated angioedema of unidentified cause.

[3] the compound, or a pharmaceutically acceptable salt, or solvate thereof, for use according to [1] or [2], wherein the angioedema is type I HAE, type II HAE, or type III HAE, preferably type I HAE or type II HAE;

[4] the compound, or a pharmaceutically acceptable salt, or solvate thereof, for use according to any one of [1] to [4], wherein the method of treating AE is on-demand treatment of an acute AE attack, preferably an acute HAE attack;

[5] the compound, or a pharmaceutically acceptable salt, or solvate thereof, for use according to [4], wherein the acute HAE attack is an acute HAE laryngeal attack;

[6] the compound, or a pharmaceutically acceptable salt, or solvate thereof, for use according to [1] to [5], wherein the compound, or a pharmaceutically acceptable salt, or solvate thereof, is administered once, twice, or three times;

[7] the compound, or a pharmaceutically acceptable salt, or solvate thereof, for use according to any one of [4] to [6], wherein the compound is administered as a single dose or as at least two doses in a dosing interval with at least 2 to 12 hours between the first dosing and the at least second dosing in said dosing interval; preferably two doses spaced at least 2, 3, 4, 5, 6, 7, 8, 9, 10, 11 or 12 hours apart, more preferably two doses spaced at least 4, 6, 8, 10 or 12 hours apart;

[8] the compound, or a pharmaceutically acceptable salt, or solvate thereof, for use according to [7], wherein the amount of the compound, or a pharmaceutically acceptable salt, or solvate thereof, in each of the at least two doses is less than the amount in the single dose;

[9] the compound, or a pharmaceutically acceptable salt, or solvate thereof, for use according to any one of [4] to [8], wherein the compound, or a pharmaceutically acceptable salt, or solvate thereof, is administered at a dose equivalent to an amount of the compound of 1 to 50 mg; 2 to 40 mg; 3 to 30 mg; 4 to 20 mg; 5 to 18 mg or 6 to 15 mg; preferably a dose of 5 mg, 6 mg, 7 mg, 8 mg, 9 mg, 10 mg, 11 mg, 12 mg, 13 mg, 14 mg, 15 mg, 17 mg, 20 mg, 22 mg, 25 mg, 27.5 mg or 30 mg; more preferably a dose of 20 to 30 mg, 20 mg or 30 mg;

[10] the compound, or a pharmaceutically acceptable salt, or solvate thereof, for use according to any one of [4] to [8], wherein the compound, or a pharmaceutically acceptable salt, or solvate thereof, is administered at a dose equivalent to an amount of the compound of at least 10 mg, at least 20 mg, at least 30 mg, at least 40 mg, or at least 50 mg;

[11] the compound, or a pharmaceutically acceptable salt, or solvate thereof, for use according to any one of [4] to [10], wherein the compound, or a pharmaceutically acceptable salt, or solvate thereof, is administered at a dose that provides a $C_{12h}$ blood or blood plasma level of the compound of at least 10 ng/mL, at least 15 ng/mL, at least 20 ng/mL, at least 25 ng/mL, at least 30 ng/mL, at least 35 ng/mL, at least 40 ng/mL, at least 45 ng/ml or at least 50 ng/ml;

[12] the compound, or a pharmaceutically acceptable salt, or solvate thereof, for use according to any one of [1] to [3], wherein the use is prophylactic treatment of AE, preferably prophylactic treatment of HAE;

[13] the compound, or a pharmaceutically acceptable salt, or solvate thereof, for use according to any one of [1] to [3], wherein the use is short-term prophylactic treatment of AE, preferably short-term prophylactic treatment of HAE;

[14] the compound, or a pharmaceutically acceptable salt, or solvate thereof, for use according to [12] or [13], wherein the compound is administered once per day, at least two times daily, or in a dosing interval, wherein each dose is spaced at least two days apart;

[15] the compound, or a pharmaceutically acceptable salt, or solvate thereof, for use according to any one of to [14], wherein the compound is administered once per day as a single dose, in two doses, three doses, or more than three doses; preferably once per day as a single dose or in two doses, more preferably once per day as a single dose;

[16] the compound, or a pharmaceutically acceptable salt, or solvate thereof, for use according to any one of to [14], wherein the compound is administered at least two times daily, wherein each dose is spaced at least 4 hours apart, at least 6 hours apart, at least 8 hours apart, at least 10 hours apart, or at least 12 hours apart;

[17] the compound, or a pharmaceutically acceptable salt, or solvate thereof, for use according to any one of to [14], wherein the compound is administered in a dosing interval, wherein each dose is spaced at least two days apart, at least three days apart, at least four days, at least five days apart, at least six days, or at least seven days apart;

[18] the compound, or a pharmaceutically acceptable salt, or solvate thereof, for use according to any one of [12] to [17], wherein the compound, or a pharmaceutically acceptable salt, or solvate thereof, is administered at a daily dose equivalent to an amount of the compound of at least 0.1 mg, at least 0.5 mg, at least 1 mg, at least 2 mg, at least 5 mg, at least 10 mg, at least 20 mg, at least 30 mg, at least 40 mg, at least 50 mg, at least 60 mg, at least 70 mg, at least 80 mg, at least 90 mg, or at least 100 mg; preferably at a daily dose equivalent to an amount of the compound of 0.1 to 100 mg, I to 90 mg, 2 to 80 mg, 3 to 70 mg, 4 to 60 mg or 5 to 50 mg;

[19] the compound, or a pharmaceutically acceptable salt, or solvate thereof, for use according to any one of to or [16], wherein the compound, or a pharmaceutically acceptable salt, or solvate thereof, is administered two times daily, wherein each dose comprises an amount of the compound equivalent to at least 0.1 mg, at least 0.5 mg, at least 1 mg, at least 2 mg, at least 5 mg, at least 10 mg, at least 20 mg, at least 30 mg, at least 40 mg, at least 50 mg, at least 60 mg, at least 70 mg, at least 80 mg, at least 90 mg, or at least 100 mg; preferably at a daily dose equivalent to an amount of the compound of 0.1 to 100 mg, 1 to 90 mg, 2 to 80 mg, 3 to 70 mg, 4 to 60 mg or 5 to 50 mg;

[20] the compound, or a pharmaceutically acceptable salt, or solvate thereof, for use according to any one of to [19], wherein the compound, or a pharmaceutically acceptable salt, or solvate thereof, is administered at a daily dose that provides a $C_{12h}$ blood or blood plasma level of the compound of at least 10 ng/mL, at least 15 ng/mL, at least 20 ng/mL, at least 25 ng/mL, at least 30 ng/mL, at least 30 ng/ml, at least 35 ng/ml, at least 40 ng/mL, at least 45 ng/ml or at least 50 ng/ml;

[21] the compound, or a pharmaceutically acceptable salt, or solvate thereof, for use according to any one of to [20], wherein the compound, or a pharmaceutically acceptable salt, or solvate thereof, is administered at a daily dose that provides a threshold blood or blood plasma level of at least 10 ng/ml, at least 15 ng/mL, at least 20 ng/ml, at least 25 ng/ml, at least 30 ng/mL, at least 35 ng/mL, at least 40 ng/mL, at least 45 ng/ml or at least 50 ng/ml;

[21A] the compound, or a pharmaceutically acceptable salt, or solvate thereof, for use according to any one of to [21], wherein the compound, or a pharmaceutically acceptable salt, or solvate thereof, is administered at a daily dose that provides a trough blood or blood plasma level equal to or greater than 10 ng/mL, 15 ng/ml, 20 ng/ml, 25 ng/ml, 30 ng/mL, 35 ng/mL, 40 ng/mL, 45 ng/ml or 50 ng/mL;

[22] the compound, or a pharmaceutically acceptable salt, or solvate thereof, for use according to [21] or [21A], wherein the threshold, or trough, blood or blood plasma level is maintained for 4 hours or more; preferably maintained for at least 4 hours, at least 6 hours, at least 8 hours, at least 12 hours or at least 24 hours;

[23] the compound, or a pharmaceutically acceptable salt, or solvate thereof, for use according to any one of [1] to [22], wherein the compound, or a pharmaceutically acceptable salt, or solvate thereof, is administered as a unit dosage form that is selected from a solution, dispersion, suspension, and a solid oral dosage form;

[24] the compound, or a pharmaceutically acceptable salt, or solvate thereof, for use according to any one of [1] to [23], wherein the compound, or a pharmaceutically acceptable salt, or solvate thereof, is administered in the form of a solid oral dosage form selected from a tablet, pill and capsule;

[25] the compound, or a pharmaceutically acceptable salt, or solvate thereof, for use according to any one of [1] to [23], wherein the compound, or a pharmaceutically acceptable salt, or solvate thereof, is administered in the form of a solution, an oral dispersion, or an oral suspension;

[25A] the compound, or a pharmaceutically acceptable salt, or solvate thereof, for use according to any one of [1] to [25], wherein the compound of formula (I) is comprised in a pharmaceutical unit dosage form in an amount of 0.1 to 100 mg, 0.5 to 90 mg, 1 to 80 mg, 2 to 75 mg, 2.5 to 70 mg, 3 to 60 mg, 4 to 50 mg; preferably 1 to 50, 60, 70, 80, 90 or 100 mg, including, for example, 2 to 35 mg, 2.5 to 30 mg, 5 mg, 10 mg, 12.5 mg, 15 mg, 17.5 mg, 20 mg, 22.5 mg, 25 mg, 27.5 mg, 30 mg, 35 mg, 40 mg, 45 mg or 50 mg;

[26] the compound, or a pharmaceutically acceptable salt, or solvate thereof, for use according to any one of [1] to [25A], wherein at least one additional therapeutic agent is co-administered;

[27] the compound, or a pharmaceutically acceptable salt, or solvate thereof, for use according to [26], wherein the at least one additional therapeutic agent is co-administered in a separate unit dosage form;

the compound, or a pharmaceutically acceptable salt, or solvate thereof, for use according to or [28], wherein the at least one additional therapeutic agent is co-administered concurrently, sequentially, alternatingly or separately;

the compound, or a pharmaceutically acceptable salt, or solvate thereof, for use according to any one of to [29], wherein the additional therapeutic agent is a CYP3A4 inhibitor, or a pharmaceutically acceptable salt, or solvate thereof; preferably a CYP3A4 inhibitor selected from the group comprising itraconazole, clarithromycin, erythromycin, telithromycin, nefazodone, voriconazole, ketoconazole, atazanavir, darunavir, indinavir, lopinavir, nelfinavir, ritonavir, saquinavir, tipranavir, cobicistat, troleandomycin, telaprevir, danoprevir, elvitegravir, mifepristone, mibefradil, LCL161, posaconazole, grapefruit juice DS, ceritinib, conivaptan, tucatinib, ribociclib, idelalisib and boceprevir, erythromycin, fluconazole, atazanavir/ritonavir, darunavir, ACT-539313, duvelisib, diltiazem, darunavir/ritonavir, dronedarone, crizotinib, atazanavir, fedratinib, letermovir, GSK2647544, aprepitant, lefamulin, casopitant, amprenavir, faldaprevir, imatinib, verapamil, ravuconazole, netupitant, nilotinib, istradefylline, grapefruit juice, tofisopam, cyclosporine, ACT-178882, ciprofloxacin, voxelotor, *Magnolia* vine (*Schisandra sphenanthera*), isavuconazole, cimetidine, FK1706, fenebrutinib, tabimorelin, amlodipine, rimegepant, ranolazine, breviscapine, lomitapide, fosaprepitant (IV), Seville orange (*Citrus aurantium*) juice, amiodarone, larotrectinib, diosmin, chlorzoxazone, M100240, fluvoxamine, ranitidine, goldenseal, clotrimazole, olaparib, tacrolimus, ASP8477, palbociclib, cilostazol, ticagrelor, peppermint oil, ivacaftor, GSK2248761, Guan Mai Ning, entrectinib, osilodrostat, AZD2327, piperine, resveratrol, roxithromycin, suvorexant, propiverine, isoniazid, berberine, hormonal contraceptives, delavirdine, daclatasvir, simeprevir, SCY-078 (MK-3118), atorvastatin, tolvaptan, rucaparib, almorexant, GSK1292263, evacetrapid, linagliptin, grazoprevir (ingredient of Zepatier), lacidipine, cranberry juice, pazopanib, fostamatinib, everolimus, blueberry juice, flibanserin, lapatinib, brodalumab, AMD070, alprazolam, Tong Xin Luo, glecaprevir and pibrentasvir, bicalutamide, sitaxentan, azithromycin, lumateperone, obeticholic acid, ginkgo, teriflunomide, or a pharmaceutically acceptable salt, or solvate thereof;

[31] the compound for use according to [30], wherein the CYP3A4 inhibitor is selected from the group comprising itraconazole, clarithromycin, erythromycin, telithromycin, nefazodone, voriconazole, ketoconazole, atazanavir, darunavir, indinavir, lopinavir, nelfinavir, ritonavir, saquinavir, tipranavir, cobicistat, troleandomycin, telaprevir, danoprevir, elvitegravir, mifepristone, mibefradil, LCL161, posaconazole, grapefruit juice DS, ceritinib, conivaptan, tucatinib, ribociclib, idelalisib and boceprevir, or a pharmaceutically acceptable salt, or solvate thereof;

[32] a kit containing: (i) a pharmaceutical unit dosage composition comprising a therapeutically effective amount of the compound of formula (I) or a pharmaceutically acceptable salt, or solvate thereof; and (ii) a pharmaceutical unit dosage composition comprising a therapeutically effective amount of a CYP3A4 inhibitor, or a pharmaceutically acceptable salt, or solvate thereof;

[33] the kit of for use as a medicament;

[34] the kit of for use in prophylactic treatment of angioedema (AE) or in a method of treating AE;

[35] the kit for use as in or [34], wherein the kit is for simultaneous, sequential, alternating or separate administration of (i) and (ii);

[36] the kit for use as in or [35], wherein (i) is used in accordance with any of [1] to [26];

[37] a method of treating or preventing a bradykinin-mediated disorder in a human comprising orally administering to the human with a bradykinin-mediated disorder a compound having the following structural formula (I):

(I)

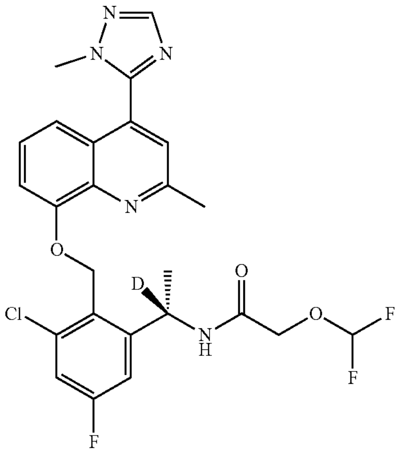

or a pharmaceutically acceptable salt, or solvate thereof; at a daily dose of at least 0.1 mg of the compound having structural formula (I);

[38] the method of [37], wherein the bradykinin-mediated disorder is angioedema (AE);

[39] the method of [38], wherein the angioedema (AE) is hereditary angioedema (HAE), acquired angioedema (AAE), bradykinin-mediated non-histaminergic idiopathic angioedema, allergic angioedema, or drug-induced angioedema, or bradykinin-mediated angioedema of unidentified cause;

[40] the method of [39], wherein the hereditary angioedema (HAE) is type I HAE, type II HAE, or type III HAE, preferably type I HAE, type II HAE;

[41] The method of or [40], wherein preventing HAE comprises reducing the frequency of HAE attacks, the severity of HAE attacks, or both;

[42] the method of or [40], wherein preventing HAE comprises the prevention of recurrent attacks of HAE;

[43] the method of or [40], wherein treating or preventing HAE comprises reducing the frequency of HAE attacks, reducing the severity of HAE attacks, improving the quality of life, reducing or eliminating the need for additional standard of care treatments for HAE, reducing the need to discontinue other treatment due to HAE, or combinations thereof;

[44] the method of [43], wherein improving the quality of life comprises improvements in self-report outcome measures;

[45] the method of any one of [37]-[45], wherein the compound is administered on-demand, daily, or both;

[46] the method of or [40], wherein preventing HAE comprises the prevention of recurrent attacks of HAE and the compound, or a pharmaceutically acceptable salt, or solvate thereof is administered daily at least once, at least twice, or at least three times;

[47] the method of [46], wherein the compound, or a pharmaceutically acceptable salt, or solvate thereof, is administered once per day, at least two times daily, or in a dosing interval, wherein each dose is spaced at least two days apart;

[48] the method of [46], wherein the compound, or a pharmaceutically acceptable salt, or solvate thereof, is administered at least two times daily, wherein each dose is spaced at least 4 hours apart, at least 6 hours apart, at least 8 hours apart, at least 10 hours apart, or at least 12 hours apart;

[49] The method of [46], wherein the compound, or a pharmaceutically acceptable salt, or solvate thereof, is administered in a dosing interval, wherein each dose is spaced at least two days apart, at least three days apart, at least four days, at least five days apart, at least six days, or at least seven days apart;

[50] the method of any one of [37]-[49], wherein the compound, or a pharmaceutically acceptable salt, or solvate thereof, is administered at a daily dose that provides a $C_{12h}$ blood or blood plasma level of the compound of at least 10 ng/ml, at least 15 ng/mL, at least 20 ng/ml, at least 25 ng/ml, at least 30 ng/ml, at least 35 ng/mL, at least 40 ng/ml, at least 45 ng/ml or at least 50 ng/ml;

[51] the method of any one of [37]-[50], wherein the compound, or a pharmaceutically acceptable salt, or solvate thereof, is administered at a daily dose that provides a threshold blood or blood plasma level of at least 10 ng/mL, at least 15 ng/mL, at least 20 ng/mL, at least 25 ng/ml, at least 30 ng/ml, at least 35 ng/mL, at least 40 ng/ml, at least 45 ng/ml or at least 50 ng/ml;

[52] the method of any one of [37]-[51], wherein the compound, or a pharmaceutically acceptable salt, or solvate thereof, is administered at a daily dose that provides a trough blood or blood plasma level equal to or greater than 10 ng/mL, 15 ng/ml, 20 ng/mL, 25 ng/ml, 30 ng/mL, 35 ng/ml, 40 ng/mL, 45 ng/ml or 50 ng/ml;

[53] The method of or [52], wherein the threshold or trough blood or blood plasma level is maintained for 4 hours or more; preferably maintained for at least 4 hours, at least 6 hours, at least 8 hours, at least 12 hours or at least 24 hours;

[54] the method of any one of [37]-[53], wherein the compound, or a pharmaceutically acceptable salt, or solvate thereof, is administered at a daily dose equivalent to an amount of the compound of at least 0.1 mg, at least 0.5 mg, at least 1 mg, at least 2 mg, at least 5 mg, at least 10 mg, at least 20 mg, at least 30 mg, at least 40 mg, at least 50 mg, at least 60 mg, at least 70 mg, at least 80 mg, at least 90 mg, or at least 100 mg; preferably at a daily dose equivalent to an amount of the compound of 0.1 to 100 mg, 1 to 90 mg, 2 to 80 mg, 3 to 70 mg, 4 to 60 mg or 5 to 50 mg;

[55] the method of any one of [37]-[53], wherein the compound, or a pharmaceutically acceptable salt, or solvate thereof, is administered once daily at dose equivalent to an amount of the compound of at least 0.1 mg, at least 0.5 mg, at least 1 mg, at least 2 mg, at least 5 mg, at least 10 mg, at least 20 mg, at least 30 mg, at least 40 mg, at least 50 mg, at least 60 mg, at least 70 mg, at least 80 mg, at least 90 mg, or at least 100 mg; preferably an amount of the compound of 0.1 to 100 mg, 1 to 90 mg, 2 to 80 mg, 3 to 70 mg, 4 to 60 mg or 5 to 50 mg;

[56] the method of any one of [46]-[53], wherein the compound, or a pharmaceutically acceptable salt, or solvate thereof, is administered at least two times daily, wherein each dose comprises an amount of the compound equivalent to at least 0.1 mg, at least 0.5 mg, at least 1 mg, at least 2 mg, at least 5 mg, at least 10 mg, at least 20 mg, at least 30 mg, at least 40 mg, at least 50 mg, at least 60 mg, at least 70 mg, at least 80 mg, at least 90 mg, or at least 100 mg; preferably an amount of the compound of 0.1 to 100 mg, 1 to 90 mg, 2 to 80 mg, 3 to 70 mg, 4 to 60 mg or 5 to 50 mg10 mg, at least 20 mg, at least 30 mg, at least 40 mg, or at least 50 mg;

[57] the method of any one of [37]-[56], wherein the compound, or a pharmaceutically acceptable salt, or solvate thereof, is administered in the form of a solution, dispersion, suspension, and a solid oral dosage form;

[58] the method of any one of [37]-[57], wherein the compound, or a pharmaceutically acceptable salt, or solvate thereof, is administered in the form of a solid oral dosage form selected from a tablet, pill and capsule;

[59] the method of any one of [37]-[57], wherein the compound, or a pharmaceutically acceptable salt, or solvate thereof, is administered in the form of an oral solution, oral dispersion, or oral suspension;

[60] the method of any one of [37]-[59], wherein the method further comprises co-administration of at least one additional therapeutic agent;

[61] the method of [60], wherein the at least one additional therapeutic agent is co-administered in a separate unit dosage form;

[62] the method of or [61], wherein the at least one additional therapeutic agent is co-administered concurrently, sequentially, alternatingly or separately;

[63] the method of any one of [60]-[62], wherein the additional therapeutic agent is a CYP3A4 inhibitor, or a pharmaceutically acceptable salt, or solvate thereof; preferably a CYP3A4 inhibitor selected from the group comprising itraconazole, clarithromycin, erythromycin, telithromycin, nefazodone, voriconazole, ketoconazole, atazanavir, darunavir, indinavir, lopinavir, nelfinavir, ritonavir, saquinavir, tipranavir, cobicistat, troleandomycin, telaprevir, danoprevir, elvitegravir, mifepristone, mibefradil, LCL161, posaconazole, grapefruit juice DS, ceritinib, conivaptan, tucatinib, ribociclib, idelalisib and boceprevir, erythromycin, fluconazole, atazanavir/ritonavir, darunavir, ACT-539313, duvelisib, diltiazem, darunavir/ritonavir, dronedarone, crizotinib, atazanavir, fedratinib, letermovir, GSK2647544, aprepitant, lefamulin, casopitant, amprenavir, faldaprevir, imatinib, verapamil, ravuconazole, netupitant, nilotinib, istradefylline, grapefruit juice, tofisopam, cyclosporine, ACT-178882, ciprofloxacin, voxelotor, Magnolia vine (*Schisandra sphenanthera*), isavuconazole, cimetidine, FK1706, fenebrutinib, tabimorelin, amlodipine, rimegepant, ranolazine, breviscapine, lomitapide, fosaprepitant (IV), Seville orange (*Citrus aurantium*) juice, amiodarone, larotrectinib, diosmin, chlorzoxazone, M100240, fluvoxamine, ranitidine, goldenseal, clotrimazole, olaparib, tacrolimus, ASP8477, palbociclib, cilostazol, ticagrelor, peppermint oil, ivacaftor, GSK2248761, Guan Mai Ning, entrectinib, osilodrostat, AZD2327, piperine, resveratrol, roxithromycin, suvorexant, propiverine, isoniazid, berberine, hormonal contraceptives, delavirdine, daclatasvir, simeprevir, SCY-078 (MK-3118), atorvastatin, tolvaptan, rucaparib, almorexant, GSK1292263, evacetrapid, linagliptin, grazoprevir (ingredient of Zepatier), lacidipine, cranberry juice, pazopanib, fostamatinib, everolimus, blueberry juice, flibanserin, lapatinib, brodalumab, AMD070, alprazolam, Tong Xin Luo, glecaprevir and pibrentasvir, bicalutamide, sitaxentan, azithromycin, lumateperone, obeticholic acid, ginkgo, teriflunomide, or a pharmaceutically acceptable salt, or solvate thereof;

[64] the method of [63], wherein the CYP3A4 inhibitor is selected from the group comprising itraconazole, clarithromycin, erythromycin, telithromycin, nefazodone, voriconazole, ketoconazole, atazanavir, darunavir, indinavir, lopinavir, nelfinavir, ritonavir, saquinavir, tipranavir, cobicistat, troleandomycin, telaprevir, danoprevir, elvitegravir, mifepristone, mibefradil, LCL161, posaconazole, grapefruit juice DS, ceritinib, conivaptan, tucatinib, ribociclib, idelalisib and boceprevir, or a pharmaceutically acceptable salt, or solvate thereof.

The compound of formula (I) for use in the prophylaxis or treatment of AE, or in the methods of prophylactic or on-demand treatement of AE attacks, according to the present invention is associated with numerous advantages when compared to known therapeutics for the treatment of AE in general and treatment of HAE, especially acute HAE in particular. Adavantages of the present invention in comparison to the sole currently available BK B2 receptor antagonist icatibant, which is administered by subcutaneous injection, include, for example, higher species selectivity, superior potency, superior pharmacological activity (prolonged efficacy), increased patient convenience due to oral availability (no injection needed), and significantly reduced treatment burden (fewer administrations, lower doses, exclusion of injection-site reactions).

The present invention is now further illustrated by the following examples from which further features, embodiments and advantages of the present invention may be taken. However, the invention should not be construed to be limited to the examples, but relates to the subject-matter defined in the claims.

EXAMPLES

Materials

Except were stated otherwise, bradykinin (BK) was purchased from Bachem Bioscience (Torrance, CA) and icatibant from Phoenix Pharmaceuticals (Burlingame, CA). The compound of formula (I) was prepared as described in WO 2019/101906 and, where necessary, under Good Manufacturing Practice (GMP) regulations. A qualified person performed the final release of the study drug, i.e. the compound of formula (I), according to Directive 2003/94/EC annex 13; and study drug labels contained information to meet the applicable regulatory requirements. Trial medication was packed, labelled and released under the responsibility of the pharmacist of the clinical site in accordance with GMP practice guidelines, International Conference on Harmonization (ICH), Good Clinical Practice (GCP) and applicable local laws/regulations. Other compounds and drugs used in the trials were commercially available, obtained from the respective manufacturer or an official supplier, and used in accordance with the protocol and the manufacturers 'summary of product characteristics (SPCs).

All studies reported herein were carried out in accordance with corresponding protocols, current guidelines on Good Clinical Practice (GCP) of the International Council for Harmonisation of Technical Requirements for Pharmaceuticals for Human Use (ICH), and applicable regulatory and country-specific governmental rules for conducting clinical trials, including rules on the protection of subjects and informed consent, and transparency requirements. All trial protocols, suitability of the investigator(s), facilities and the methods and material to be used in obtaining and documenting informed consent of the trial subject were reviewed and approved by the Institutional Review Board (IRB) or Independent Ethics Committee (IEC) before a study was started.

Abbreviations used in the following examples include:

AUC area under the plasma concentration-time curve $AUC_{last}$ AUC from time 0 to the time of the last measurable (non-below quantification limit) concentration, calculated by linear-linear trapezoidal summation;

$AUC_{inf}/AUC_{\infty}$ AUC from time 0 to infinite time, calculated as $AUC_{last}+C_{last}/\lambda_z$, where $C_{last}$ is the last observed measurable (non-below-quantification limit) concentration; extrapolations of more than 20% of the total AUC are reported as approximations;

b.i.d. twice daily

BQL below quantification limit $Ca_{vg}$ average steady-state plasma concentration CI confidence interval CL/F apparent total clearance, calculated as dose/$AUC_{\infty}$;

$C_{max}$ maximum observed analyte concentration $C_{min}$ minimum observed analyte concentration $C_{trough}$ observed analyte concentration just prior to the beginning or at the end of a dosing interval CV coefficient of variation $\lambda_z$ apparent terminal elimination rate-constant estimated by linear regression using the terminal log-linear phase of the log transformed concentration vs. time curve;

LLOQ lower limit of quantification

NA not assessable

PD pharmacodynamic

PK pharmacokinetic q.d. once daily $r^2_{adj}$ coefficient of determination

SD standard deviation $\tau$ dosing interval $t_{1/2}$ apparent terminal elimination half-life; calculated as $0.693/\lambda_z$;

$t_{lag}$ time period between the time of dosing and the time of the first measurable (non-BQL) concentration $t_{max}$ actual sampling time to reach the maximum observed analyte concentration.

$V_z/F$ apparent volume of distribution, calculated as dose/($\lambda z*AUC_{\infty}$).

Example 1

Species Selectivity

The bradykinin B2 receptor is well known for its species selective pharmacology (Paquet et al., Br. J. Pharmacol. (126), 1083-1090, 1999 (DOI: 10.1038/sj.bjp.0702403); Burgess et al., Br. J. Pharmacol. (129), 77-86, 2000 (DOI: 10.1038/sj.bjp.0703012)). The antagonist potency of the compound of formula (I) in cells expressing B2 receptors from human, cynomolgus monkey, dog, rat, and mouse was determined as described in Lesage et al., Front. Pharmacol. 11:916; DOI: 10.3389/fphar.2020.00916. The Kb value (nM) of the compound of formula (I) to antagonize BK activation of the cynomolgus monkey B2 receptor was found to be in the same range as for the human B2 receptor (1.42 nM versus 0.15 nM). The compound of formula (I) was however more than 1000-fold less potent in antagonizing the rat B2 receptor, more than 3000-fold less potent towards the mouse B2 receptor, and 18,000-fold less potent towards the dog B2 receptor. In contrast, icatibant showed a more or less stable antagonist potency across species (3.19 nM (human B2 receptor); 4.06 nM (cynomolgus monkey B2 receptor); 5.6 nM (rat B2 receptor); 4.40 nM (mouse B2 receptor) and 30.7 nM (dog B2 receptor). In addition, it was found that the compound of formula (I) is devoid of intrinsic agonist activity.

Thus, the compound of formula (I) has a higher species selectivity, and is about 20 times more potent at human B2 receptor than the sole currently available BK B2 antagonist icatibant.

Assessment of Oral Bioavailability

The objective of the study was to compare and assess the systemic exposure of the test compounds in vivo after a single oral administration in the cynomolgus monkey, in particular oral exposure and dose-proportionality in exposure.

The Test Facility for the study was Charles River Laboratories France Safety Assessment SAS, 329 Impasse du Domaine Rozier, Les Oncins, 69210 Saint-Germain-Nuelles, France. The Test Facility is AAALAC accredited and the study design was reviewed and approved by the ethical committee of the Test Facility as per the standard document "Singe_Dose unique_2015juillet02 CEA". In addition, the study design was in general compliance with the following animal health and welfare guidelines:

Guide for the care and use of laboratory animals, 2011.

Decree n° 2013-118 relating to the protection of animals used in scientific experiments described in the Journal Officiel de la République Française on 1 Feb. 2013.

Directive 2010/63/EU of the European Parliament and of the Council of 22 Sep. 2010 on the protection of animals used for scientific purposes.

The test compounds were the compound of formula (I) and compound A, (S)—N-(1-(3-chloro-5-fluoro-2-((2-methyl-4-(1-methyl-1H-1,2,4-triazol-5-yl) quinolin-8-yloxy)methyl)phenyl)ethyl)-2-(difluoromethoxy) acetamide having the following structure:

(A)

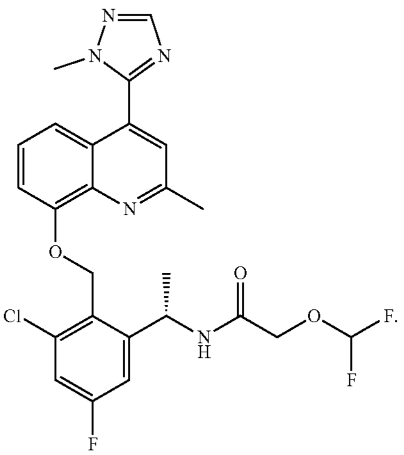

Each of the test compounds was administered to three non-naïve male monkeys via oral gavage (po) at 1 mg/kg, 5 mL/kg and 10 mg/kg, 5 mL/kg. The vehicle for the oral doses used was 25% HPBCD (Kleptose HPB, parenteral grade, Roquette) in a 10-mM phosphate buffer (Na2HPO4, pH 7 for 1 mg/kg and pH 2 or 3 for 10 mg/kg formulation), and the dose concentration was 0.2 mg/mL for the 1 mg/kg and 2 mg/mL for the 10 mg/kg formulation. The assessment of the general health status was based on morbidity/mortality, clinical observations, detailed clinical/physical examinations and body weight. The test compounds did not adversely affect the general health status or the body weight gain of the animals throughout the study period. For all animals, pharmacokinetic blood samples were taken before dosing and at 0.5, 1, 2, 3, 4, 6, 8, 12 and 24 hours after po administration.

The systemic exposure to the test compounds after oral administration was found to be dose-proportional over the dose range of 1 to 10 mg/kg in all animals for both test compounds. However, significant differences between the test compounds were found for the maximal observed mean plasma concentration ($C_{max}$ (ng/mL)) and the area under the curve extrapolated to infinity (AUC (0-inf) (ng*h/mL)). In comparison to Compound A, the compound of formula (I) showed a 308% higher $C_{max}$ 0.5-2 h after oral administration of the 10 mg/kg formulation, and the AUC (0-inf) was 186% higher compared to compound A.

These results demonstrate that the compound of formula (I) has an outstanding oral exposure, which is highly advantageous in therapeutic application as it can markedly reduce treatment burden of patients in that, for example, frequency of administrations and/or dose can be drastically lowered.

Example 2: Proof of Concept Trial in Healthy Volunteers

To assess the safety, tolerability, PK and PD of the compound of formula (I) after oral administration to healthy subjects, a randomized, double-blind, placebo-controlled, single ascending dose and proof-of-mechanism study was performed.

A total of 52 subjects received single ascending oral doses of the compound of formula (I) up to 22 mg, and 16 subjects received placebo. Table 1 below shows the tested cohorts.

TABLE 1

| Dose | Part 1 (PK) | Part 2 (PD #) |
|---|---|---|
| 1 mg * | N = 6 | |
| 2 mg * | N = 6 | |
| 4.5 mg * | N = 6 | |
| 12 mg | N = 6 | N = 8 |
| 22 mg * | N = 6 | N = 8 |
| 22 mg § | N = 6 | |
| Placebo | N = 12 | N = 4 |

* fasted condition
§ after high caloric/high fat (HCHF) breakfast

Safety was assessed by physical examination, vital signs, adverse events, safety laboratory and electrocardiogram (ECG) until 72 h post-dosing. Plasma pharmacokinetic (PK) parameters of the compound of formula (I) were assessed until 72 h postdosing.

Figure 2:
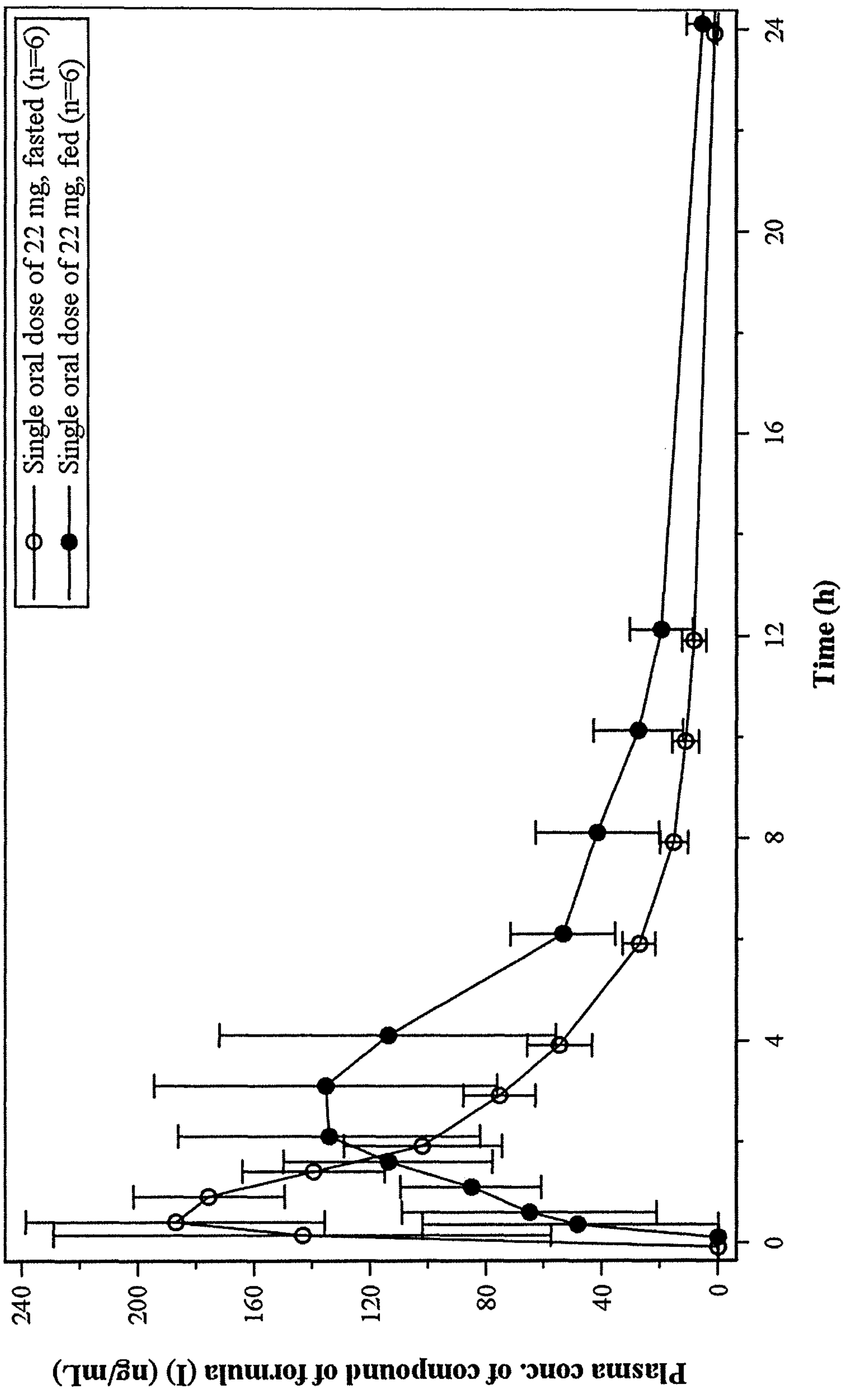
FIG. 2. Plasma levels of the compound of formula (I) observed in healthy volunteers under fasted condition and after a high caloric/high fat breakfast after oral administration of a single dose of 22 mg of the compound. Graphs display mean including standard deviation bars.

The compound was very rapidly absorbed and reached peak plasma levels within 30 to 60 minutes after dosing in all subjects under fasted conditions. The systemic exposure was dose proportional with a mean tiz ranging from 3.5 to 5.6 h between doses. Plasma levels for the compound reached therapeutic efficacious threshold concentration within 15 min for all doses and were maintained for approximately 12 h with doses of 12 mg and 22 mg. Observed plasma levels of the compound of formula (I) in cohorts under fasted conditions are shown in FIG. 1. A comparison of plasma levels of the 22 mg dose cohort under fasted condition and the 22 mg cohort with HCHF breakfast is shown in FIG. 2. Administration of the 22 mg dose of the compound after HCHF breakfast led to a 32% lower $C_{max}$, a 49% higher $AUC_{last}$, and a delay of median $t_{max}$ by approximately 2 h. However, therapeutically effective plasma levels were still reached in the HCHF breakfast cohort within 15 min and maintained for more than 12 h. Mean (±SD) $C_{12h}$ was 8.34±4.24 h and 19.6±10.7 ng/ml under fasted and fed conditions, respectively. Mean C24h was 1.12±0.786 h to 5.39±5.47 ng/mL under fasted and fed conditions, respectively.

The compound of formula (I) was safe and well tolerated when administered orally up to single doses of 22 mg. No adverse event was reported as serious, no premature withdrawals due to an adverse event occurred, and no severe adverse event was reported. In addition, no clinically relevant fluctuations of blood pressure and no orthostatic hypotension linked to the compound of formula (I) occurred. The overall incidence of adverse events was similar between the placebo groups and the groups receiving the compound of formula (I). Treatment-related adverse events were reported for three subjects who received the compound of formula (I) (12 or 22 mg), all within the gastrointestinal system and of mild severity: upper abdominal pain, vomiting, and nausea. There were no apparent trends or dose-related changes in hematology, clinical chemistry, vital signs, or ECG. Details of the safety evaluation are summarized in Table 2 below.

TABLE 2

| | Dose | | | | | | |
|---|---|---|---|---|---|---|---|
| | 1 mg * N = 6 | 2 mg * N = 6 | 4.5 mg * N = 6 | 12 mg * N = 14 | 22 mg * N = 14 | 22 mg § N = 6 | Placebo N = 16 |
| n (%) (adverse effects) | | | | | | | |
| Any | 2 (33.3%) | 1 (16.7%) | 1 (16.7%) | 5 (35.7%) | 2 (14.3%) | 1 (16.7%) | 5 (31.3%) |
| Any related | 0 | 0 | 0 | 2 (14.3%) | 1 (7.1%) | 0 | 1 (6.3%) |
| Any serious | 0 | 0 | 0 | 0 | 0 | 0 | 0 |

n and % refer to number and percentage of patients
* fasted condition
§ after HCHF breakfast Dose proportional PK was observed after single oral administration under fasting condition of the compound of formula (I) in the dose range of 1 mg to 22 mg for $C_{max}$, $AUC_{last}$ and $AUC_{inf}$. Median tmax in the dose range of 1 mg to 22 mg was between 0.50 h and 1.00 h, with comparable ranges of individual values (ranging between 0.25 h and 1.02 h). The results of the pharmacokinetic evaluation of the compound of formula (I) are summarized in Table 3 below.

of Action During Bradykinin Challenge, JACI (129), AB222 (2012); https://www.jacionline.org/article/S0091-6749 (11) 02076-8/fulltext); FDA Office of Clinical Pharmacology Review Firazyr®, Application Number 022150Origls000 (2011); https://www.accessdata.fda.gov/drugsatfda_docs/nda/2011/022150Origls000ChemR.pdf), the sole BK antagonist currently available.

TABLE 3

Pharmacokinetics of compound of formula (I)

| Dose | 1 mg * N = 6 | 2 mg * N = 6 | 4.5 mg * N = 6 | 12 mg * N = 6 | 22 mg * N = 6 | 22 mg § N = 6 |
|---|---|---|---|---|---|---|
| $C_{max}$, ng/ml | 11.1 (4.03) | 19.8 (3.70) | 32.9 (7.66) | 97.3 (28.1) | 213 (49.5) | 145 (56.2) |
| $t_{max}$, h | 0.50 (0.25-1.00) | 0.75 (0.25-1.02) | 1.00 (0.50-1.00) | 0.50 (0.25-1.00) | 0.75 (0.25-1.02) | 3.00 (2.00-3.00) |
| $C_{0.25h}$, ng/ml | 5.99 (4.28) | 12.9 (8.10) | 13.0 (7.00) | 60.3 (40.6) | 143 (85.9) | 48.3 (53.9) |
| $C_{12h}$, ng/ml | 0.528 (0.670) | 0.810 (0.619) | 1.93 (1.87) | 5.58 (5.66) | 8.34 (4.24) | 19.6 (10.7) |
| AUClast, ng · h/mL | 33.0 (25.9) | 66.0 (27.0) | 129 (56.5) | 369 (194) | 681 (113) | 1015 (490) |
| $t_{1/2}$, h | 3.49 (1.32) | 4.26 (1.91) | 4.36 (1.29) | 4.25 (0.831) | 5.61 (0.707) | 5.31 (1.54) |
| $V_z$/F, L | 190 (95.7) | 181 (34.3) | 222 (43.7) | 235 (96.3) | 252 (30.9) | 180 (51.8) |
| CL/F, L/h | 42.3 (25.4) | 33.8 (11.9) | 37.6 (11.1) | 40.9 (20.7) | 31.5 (5.60) | 25.3 (9.77) |

# means (standard deviation), median (range) for $t_{ma}$x

* fasted condition

§ after HCHF breakfast

Example 3: Bradykinin Challenge Study

Figure 3:
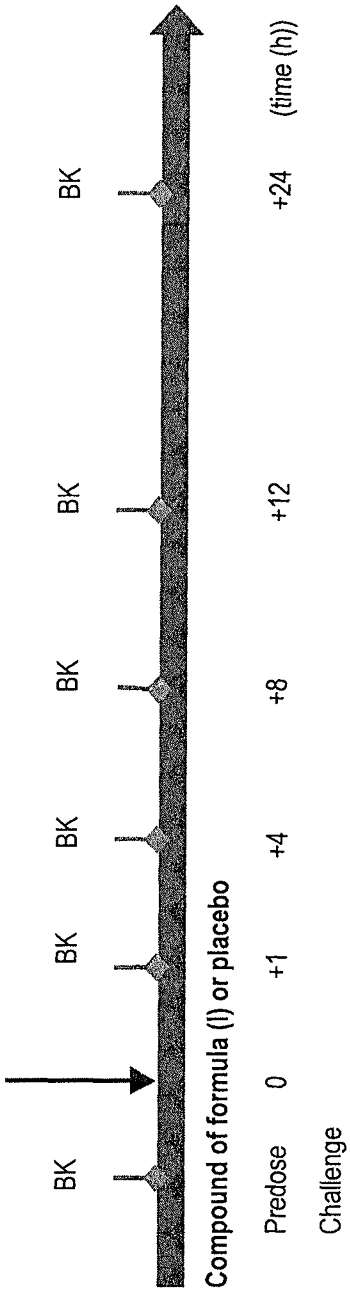
FIG. 3. Schematic Design of Bradykinin Challenge Study.

Pharmacodynamics (PD) of the compound of formula (I) were evaluated in a BK challenge model, which involves the demonstration of the inhibition of BK-mediated diastolic blood pressure drop and heart rate increase by administering BK to healthy subjects at specific intervals after administration of the compound. The bradykinin challenge is a validated surrogate assessment that was reviewed and approved by the U.S. Food and Drug Administration (FDA) and the European Medicines Agency (EMA) for phase I clinical trials in the development of icatibant. The clinical dose of icatibant established with the BK challenge has demonstrated successful resolution of HAE attacks in randomized clinical trials and over 10 years of clinical experience with icatibant. Schematic design of the BK challenge study is shown in FIG. 3.

Inhibition of BK was assessed in the BK challenge (FIG. 3) with single doses of 12 and 22 mg of the compound of formula (I). The compound (12 and 22 mg) was administered orally (p.o.) to 16 healthy volunteers. BK was injected intravenously prior to oral administration of the compound, i.e. BK predosing challenge, and at 1, 4, 8, 12 and 24 hours after oral administration (dosing) of the 12 and 22 mg single dose, respectively. BK injections were administered to induce cardiovascular responses in the volunteers. The cardiovascular responses were monitored, and blood samples were drawn over 24 hours for PK assessment. The PD outcome variables were measured from 5 min before until 5 min after each BK bolus. A % inhibition-of-the-baseline average-to-peak effect was calculated and used as the PD outcome. Table 5 below shows PK/PD parameters for inhibition of BK challenge by the compound of formula (I).

Figure 4:
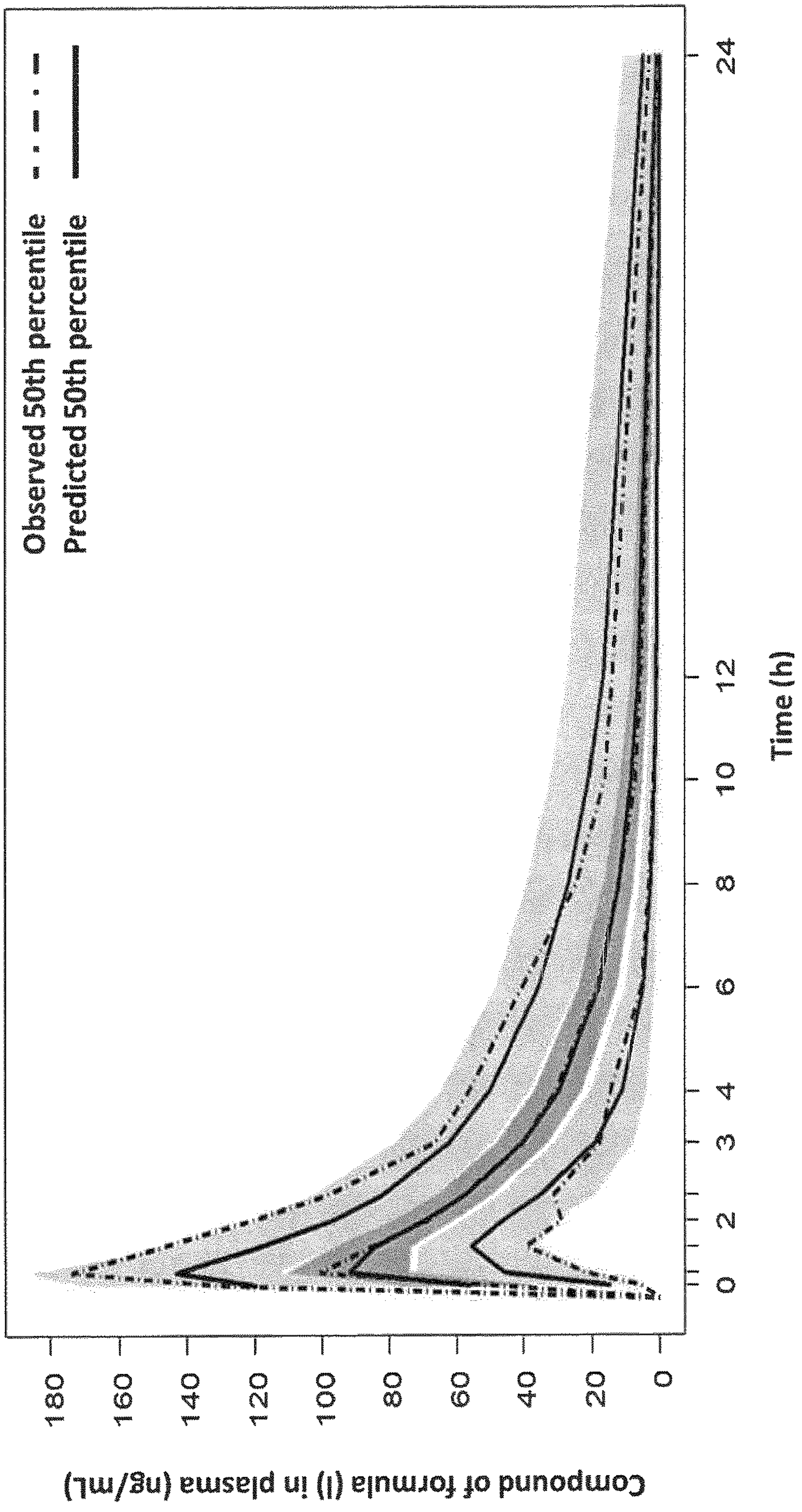
FIG. 4. Visualized pharmacokinetic profile of a single orally administered 12 mg dose of compound of formula (I) as determined in PK model. The dashed lines are the 2.5th, 50th and 97.5th percentiles of the observations. Predicted percentiles (i.e., 2.5th, 50th, and 97.5th, solid lines) with their corresponding 95% confidence intervals (blue and red shaded areas) obtained using N=1000 replicates of the dataset.
Figure 5:
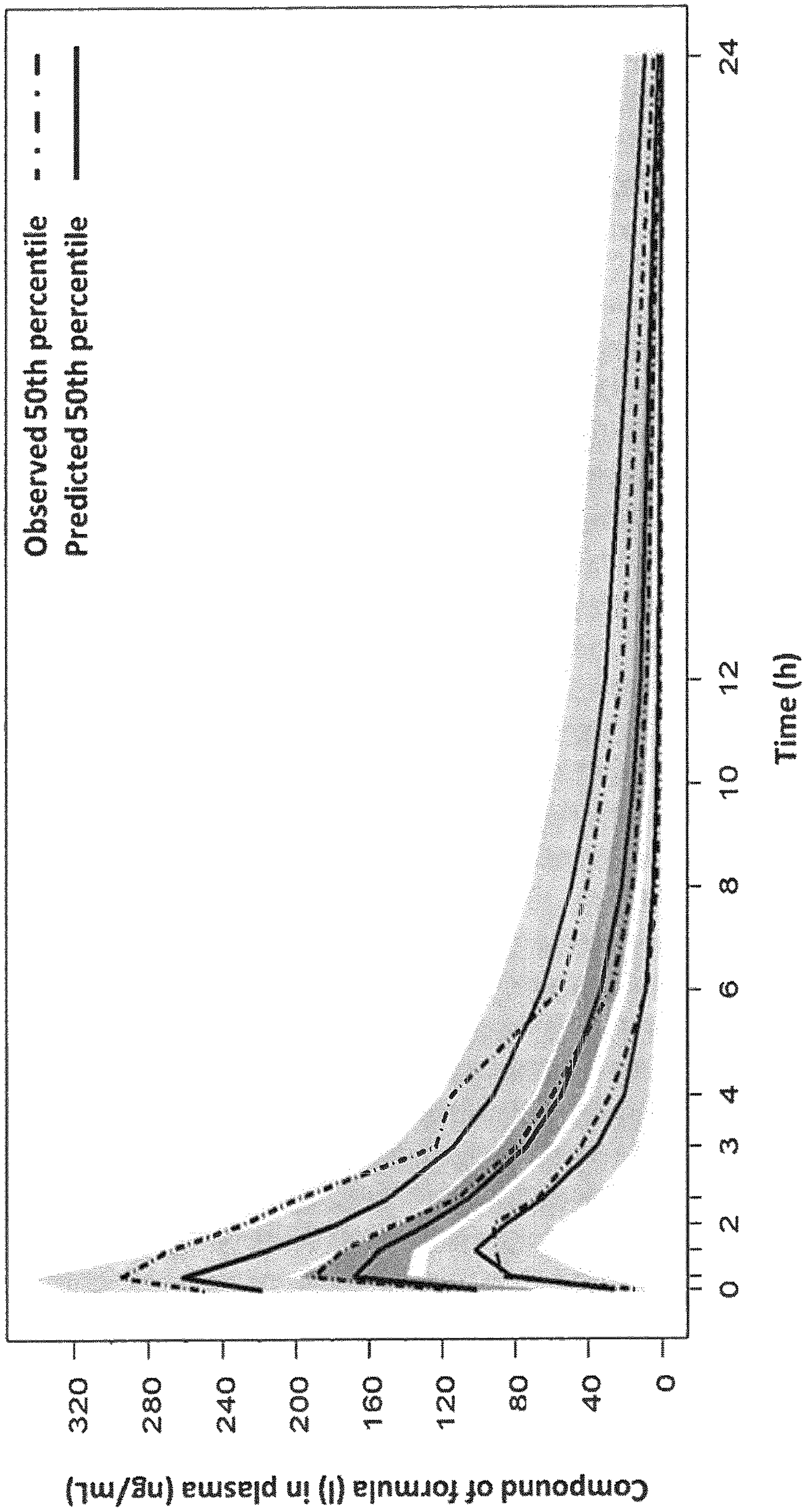
FIG. 5. Visualized pharmacokinetic profile of a single orally administered 22 mg dose of compound of formula (I) as determined in PK model. The dashed lines are the 2.5th, 50th and 97.5th percentiles of the observations. Predicted percentiles (i.e., 2.5th, 50th, and 97.5th, solid lines) with their corresponding 95% confidence intervals (blue and red shaded areas) obtained using N=1000 replicates of the dataset.
Figure 6:
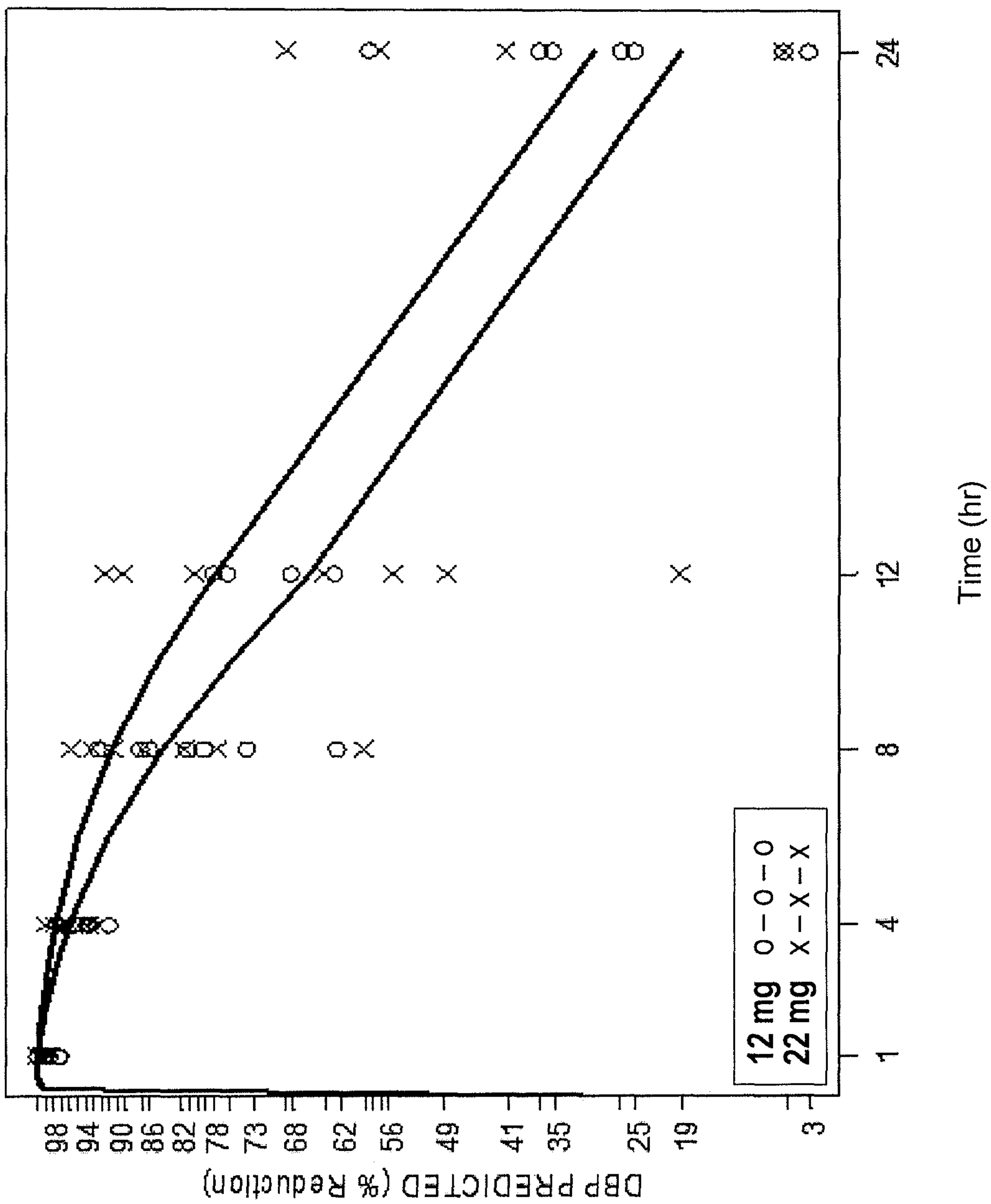
FIG. 6. Predicted effect-time profile of singly, orally administered doses (12 mg and 22 mg, respectively) of compound of formula (I) for Diabolic Blood Pressure (DBP) based on PK/PD parameters obtained in BK challenge study. Solid lines are PK and PD model predictions.
Figure 7A:
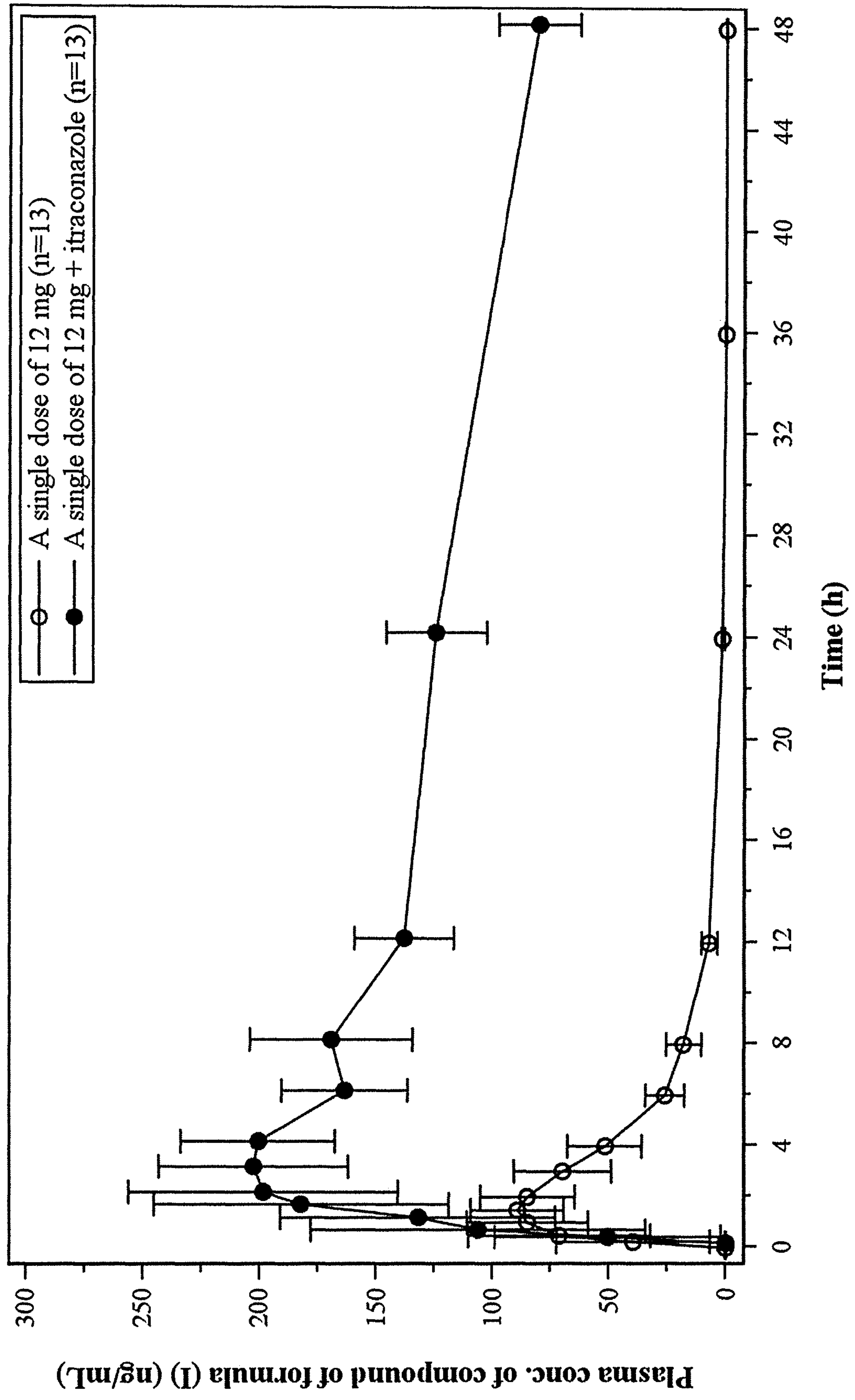
FIG. 7. A. Linear mean plasma concentration-time profiles of the compound of formula (I) (including standard deviation bars) after administration of a single 12 mg oral dose of the compound of formula (I) in the absence (Day 1) or presence (Day 7) of itraconazole* in healthy adult subjects. B. Semi-logarithmic mean plasma concentration-time profiles of the compound of formula (I) (including standard deviation bars) after administration of a single 12 mg oral dose of the compound of formula (I) in the absence (Day 1) or presence (Day 7) of itraconazole* in healthy adult subjects.
Figure 7B:
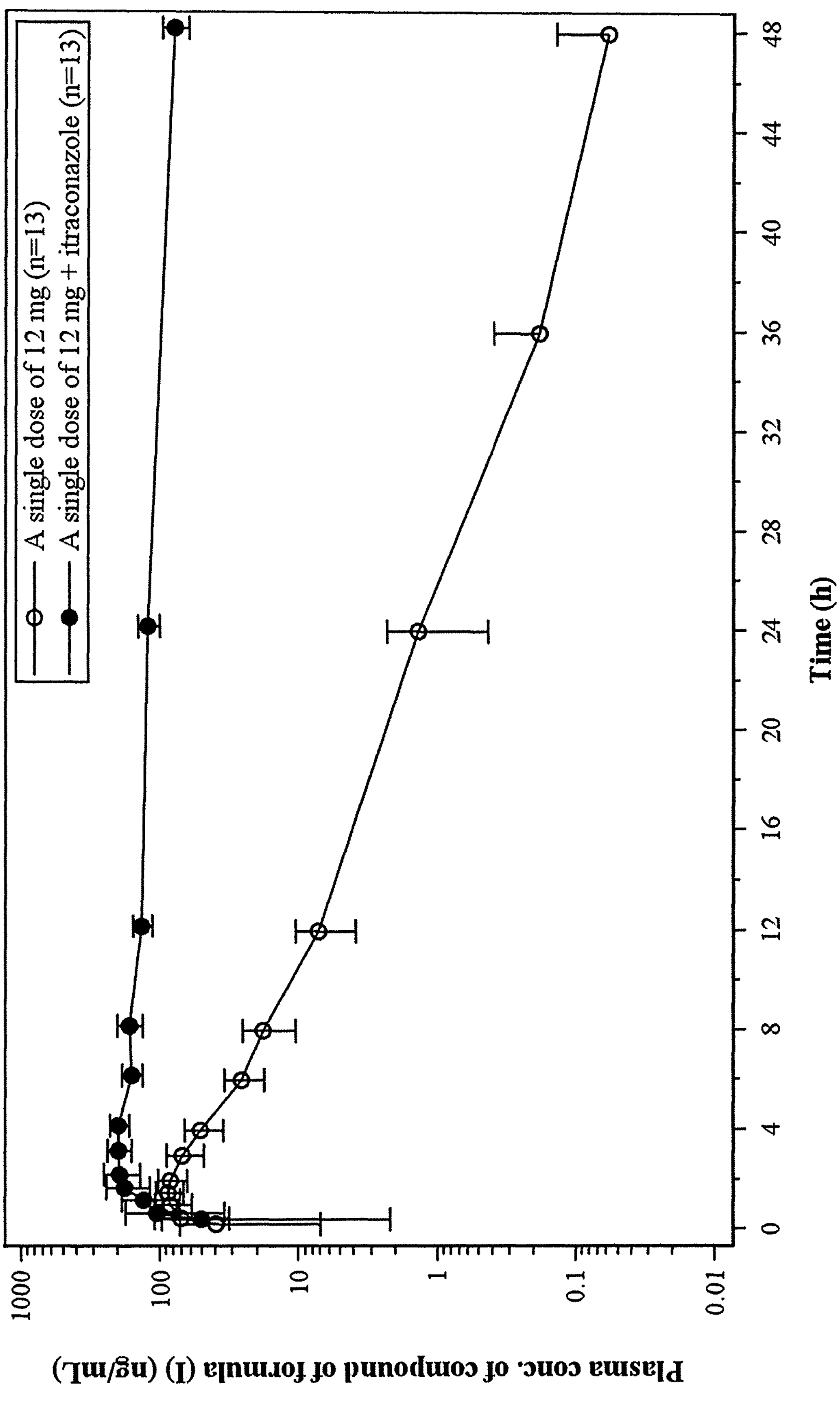

Immediately after BK injection a short-lived change in blood pressure, heart rate and cardiac output can be recorded. In presence of the compound of formula (I) this response is dampened and the degree of attenuation depends on the concentration of the compound. Dampened BK-induced effects are closely associated with successful therapeutic outcome for icatibant (Leach et al., Icatibant Duration A PK/PD analysis using the same approach as in the icatibant evaluation was conducted. In short, changes of BK responses induced by the compound of formula (I) were evaluated with a nonlinear mixed-effect PK/PD model. PK was analyzed using a two-compartment body model with first-order oral absorption and a lag time; results are shown in Table 4. For the PK/PD model a simple Emax-model with a direct link was utilized. The PK/PD model was used to simulate PK profiles (N=1000) and calculate probability of durations of effect as well as to visualize effect-time profiles; see FIGS. 4 and 5.

TABLE 4

Population 2-compartment PK model with oral absorption model parameter estimates (CV %) for the compound of formula (I)

| | |
|---|---|
| CL/F (L/h) | 34.5 (5.9%) |
| V2/F (L) | 101 (4.5%) |
| Q/F (L/h) | 10.7 (15.8%) |
| V3/F (L) | 35.9 (10.7%) |
| Ka (1/h) | 7.97 (25.1%) |
| Tlag (h) | 0.181 (9.9%) |

CL/F apparent clearance;

V2/F apparent volume for the central compartment;

Q/F apparent inter-compartmental clearance;

V3/F apparent volume for the peripheral compartment;

Ka first order absorption rate constant;

Tlag lag time

The EC50 and EC85 values estimated for each PD response associated with the BK challenge are shown in Table 5 below. The composite average shows an EC50 of 2.4 ng/mL and an EC85 of 13.8 ng/mL for the compound of formula (I). The results were compared to published results obtained for icatibant (FDA Office of Clinical Pharmacology Review Firazyr®, Application Number 022150Origls000 (2011); https://www.accessdata.fda.gov/drugsatfda_docs/nda/2011/022150Origls000ChemR.pdf), and show that the compound of formula (I) is approximately four-fold more potent than icatibant (EC50 of 9.5 ng/ml and EC85 of 53.8 ng/ml) based on plasma concentrations. The free plasma concentration associated with said EC50 value of 2.4 ng/ml (plasma protein binding 96.2%), is 170 pM, a potency that is in line with the antagonist potency of the compound of formula (I) at recombinant and endogenous human B2 receptors (150 and 350 pM, respectively). This shows that the potency of the compound of formula (I) in molar concentrations is sustained between in vitro, ex vivo and in healthy volunteers. Particularly noteworthy, the intrinsic PD potency of the compound of formula (I) at the K B2 receptor was found to be about 25-fold higher than that of icatibant (8.9 nM).

TABLE 5

Estimated EC50 and EC85 of the compound of formula (I) based on PD determined in BK challenge

| | Diastolic blood pressure | Heart rate | Cardiac output | Composite average |
|---|---|---|---|---|
| $EC_{50}$ (ng/mL) | 2.34 | 3.3 | 1.68 | 2.4 |
| $EC_{85}$ (ng/mL) | 13.26 | 18.7 | 9.52 | 13.8 |

$EC_{50}$ = estimated drug concentration for 50% of maximum response;
$EC_{85}$ = estimated drug concentration for 85% of maximum response The data also allows a comparison of the expected therapeutic performance of the compound of formula (I) with that of icatibant. It has been shown for icatibant that the therapeutic response to an acute HAE attack wanes after approximately 6 hours. This is also the time point when icatibant concentrations drop below therapeutic levels due to the short half-life (1.4h) of the drug. More precisely, it was shown for the approved 30 mg dose of icatibant that icatibant plasma concentration has a 75% probability of being 50% effective (i.e. to be above ECso) for at least 6.5 hours and a 50% probability of being 85% effective (i.e. to be above ECss) for 5.5 hours. This correlates well with clinical efficacy of icatibant (FDA Office of Clinical Pharmacology Review FirazyrR, loc. cit.; FirazyrR, Prescribing Information, https://www.shirecontent.com/PI/PDFs/Firazyr_USA_ENG.pdf). Therefore, the criteria of BK challenge data can similarly be applied as exposure targets for the compound of formula (I). Tables 6A and 6B below compares the 30 mg dose of icatibant to respective doses of 12 mg and 22 mg of the compound of formula (I) based on BK-challenge modeling and simulation.

TABLE 6A

| Response | Icatibant 30 mg s.c. | Compound of formula (I) 12 mg p.o. | Compound of formula (I) 22 mg p.o. |
|---|---|---|---|
| | Time (h) plasma level above EC50 at a 75% confidence level | | |
| DBP | 6 | 11.5 | 14 |
| MAP | 6 | 12 | 15.5 |
| HR | 6.5 | 10 | 13 |

TABLE 6B

| Response | Icatibant 30 mg s.c. | Compound of formula (I) 12 mg p.o. | Compound of formula (I) 22 mg p.o. |
|---|---|---|---|
| | Time (h) plasma level above EC85 at a 75% confidence level | | |
| DBP | 5.5 | 7.5 | 10 |
| MAP | 5.5 | 7 | 10 |
| HR | 5.5 | 6.5 | 9.5 |

As can be taken from Tables 6A and B above, the investigated doses (12 and 22 mg, respectively) of orally administered compound of formula (I) exceed the duration of effect reported for 30 mg subcutaneously injected icatibant considerably. Due to the longer half-life of the compound of formula (I), the compound of formula (I) stays above the therapeutic targets for much longer than icatibant. The 12 mg oral dose of the compound of formula (I) showed rapid absorption and then stayed above ECso for 10-12 hours and above ECss for 7 hours, suggesting that this dose is at least as effective as a 30 mg s.c. injection of icatibant. Duration of effect for the higher 22 mg oral dose was approximately twice as long, and thus equivalent to two icatibant injections 6 h apart.

In essence, a significantly higher pharmacodynamic potency as compared to published results of icatibant was observed in the responses to the compound of formula (I). The investigated single oral doses of the compound of formula (I), i.e. 12 and 22 mg, provide equivalent BK-antagonism for a longer time than a 30 mg s.c. icatibant injection. This longer duration of effect of the compound of formula (I) is highly advantageous in therapeutic application as it significantly reduces treatment burden of patients in that it drastically lowers frequency of administrations, excludes injection-site reactions (no injection needed due to oral availability), and allows for lower doses to be administered.

Example 4-Ascending Dose Study

A randomized, double-blind, placebo-controlled single ascending dose study was performed to examine the safety, tolerability, and PK of single ascending oral doses of 22, 33, and 50 mg of the compound of formula (I) in healthy volunteers after a standard caloric meal, and a single oral dose of 40 mg of the compound of formula (I) was tested in healthy volunteers under fasting conditions. A total of 32 subjects received either the compound of formula (I) (n=24) or placebo (n=8).

The study results showed that the compound of formula (I) at doses up to 40 mg under fasting and 50 mg under fed conditions was safe and well tolerated. There were no serious adverse effects reported. Treatment-related adverse effects that were reported as possibly related to the compound of formula (I) were mild nausea (22 mg), mild headache (50 mg), and moderate headache associated with vomiting (50 mg). There were no clinically significant changes in vital signs, laboratory, or ECG parameters between the placebo group and those receiving the compound of formula (I).

Over the investigated dose range from 22 to 50 mg (factor 2.27 increase) after a standardized breakfast, the compound of formula (I) showed dose-proportional PK with a 2.37-fold and 2.39-fold increase for mean $C_{max}$ and AUCo-24h, respectively. Administration of the compound of formula (I) after a standardized breakfast resulted in 40-50% decrease in $C_{max}$, but $AUC_{inf}$ did not show a significant change compared to administration under fasting conditions. $C_{12h}$ and C24h plasma concentration for the compound of formula (I) was higher under fed conditions, which is indicative of favorable effects in prophylactic treatment.

Example 5: Drug—Drug Interaction

An open-label, single sequence crossover drug-drug interaction trial was performed to evaluate the effect of multiple doses of itraconazole, a potent CYP3A4 inhibitor, at steady-state on the PK of a single dose of the compound of formula (I) in healthy subjects. In addition, the trial was carried out to evaluate the safety and tolerability of the compound of formula (I) alone and in combination with multiple doses of the CYP3 A4 inhibitor itraconazole in healthy adult subjects. Thirteen healthy subjects were enrolled and completed the study.

During the study, on Day 1, all subjects received a single 12 mg oral dose of the compound of formula (I) 0.5 hours after finishing a standard breakfast. On Day 3, subjects received 200 mg itraconazole twice daily, with approximately 12 hours in between administrations, one hour before start of a standard meal. On Days 4 to 8, subjects received once daily oral doses of 200 mg itraconazole one hour before start of a standard meal. In the morning of Day 7, subjects received a single dose of 12 mg of the compound of formula (I) 0.5 hour after finishing a standard breakfast. Therefore, the intake of the compound of formula (I) on Day I and Day 7 took place under fed conditions.

Plasma concentrations of the compound of formula (I) were determined predose and over a 48-hour evaluation period after dosing of the compound of formula (I) on Days I and 7. Trough plasma concentrations of itraconazole were determined by taking predose plasma samples on Days 4-7, to document exposure to itraconazole. It was found that the mean itraconazole predose plasma concentration ($C_{trough}$) levels increased gradually from Day 4 (386±82.2 ng/ml) to Day 7 (597±178 ng/ml). Similar observations were made for the mean hydroxyitraconazole predose plasma concentration ($C_{trough}$) levels, which increased gradually from Day 4 (730±93.5 ng/ml) to Day 7 (1187±213 ng/ml). These values are consistent with the previously published data of Hardin et al. (Pharmacokinetics of itraconazole following oral administration to normal volunteers; Antimicrob Agents Chemother. 32 (9): 1310-1313, 1988).

Administration of the single 12 mg oral doses of the compound of formula (I) on Day 1 and Day 7 was well tolerated with no related adverse events reported. Itraconazole co-administration resulted in a 2.2-fold higher $C_{max}$ and a 12-fold higher $AUC_{last}$ compared to a single 12 mg oral intake of the compound of formula (I) without itraconazole. Median tmax was shifted from 0.50-1.00 h when the compound of formula (I) was taken alone to 3.00-4.00 h when itraconazole was co-administered with the compound. The mean terminal half-life of the compound of formula (I) increased from 4.31 h when the compound was administered alone to 41.3 h when itraconazole was co-administered with the compound. All these findings are in line with in vitro data showing that the compound of formula (I) is a substrate of CYP3A4.

In essence, duration of effect of the compound of formula (I) is significantly improved in the presence of a CYP3A4 inhibitor compared administration of the compound alone. This longer duration of effect of the compound of formula (I) is highly advantageous in therapeutic application as it can markedly reduce treatment burden of patients in that frequency of administrations and/or dose can be drastically lowered.

The features of the present invention disclosed in the specification and/or the claims may both separately and in any combination thereof be material for realizing the invention in various forms thereof.

The invention claimed is:

1. A method of treating or preventing a bradykinin-mediated disorder in a human comprising orally administering to the human with a bradykinin-mediated disorder a compound having the following structural formula (I):

(I)

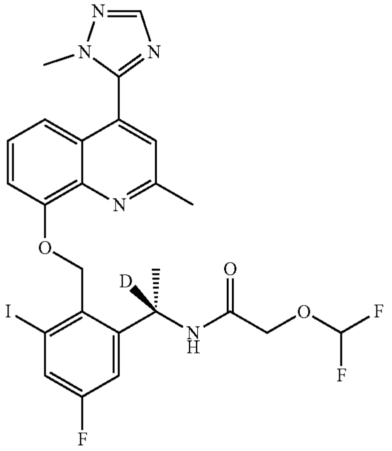

or a pharmaceutically acceptable salt, or solvate thereof: at a dose of 10 to 50 mg of the compound having structural formula (I), wherein the bradykinin-mediated disorder is angioedema (AE), and wherein the compound is administered on-demand, daily, or both.

2. The method of claim 1, wherein the angioedema (AE) is hereditary angioedema (HAE), acquired angioedema (AAE), bradykinin-mediated non-histaminergic idiopathic angioedema, allergic angioedema, or drug-induced angioedema, or bradykinin-mediated angioedema of unidentified cause.

3. The method of claim 2, wherein treating or preventing HAE comprises reducing the frequency of HAE attacks, reducing the severity of HAE attacks, the prevention of recurrent attacks of HAE, improving the quality of life, reducing or eliminating the need for additional standard of care treatments for HAE, reducing the need to discontinue other treatment due to HAE, or combinations thereof.

4. The method of claim 3, wherein preventing HAE comprises the prevention of recurrent attacks of HAE and the compound, or a pharmaceutically acceptable salt, or solvate thereof, is administered daily.

5. The method of claim 4, wherein the compound, or a pharmaceutically acceptable salt, or solvate thereof, is administered once per day or two times daily.

6. The method of claim 4, wherein the compound, or a pharmaceutically acceptable salt, or solvate thereof, is administered two times daily, wherein each dose is spaced at least 4 hours apart, at least 6 hours apart, at least 8 hours apart, at least 10 hours apart, or at least 12 hours apart.

7. The method of claim 1, wherein the compound, or a pharmaceutically acceptable salt, or solvate thereof, is administered at a daily dose that provides a $C_{12h}$ blood or blood plasma level of the compound of at least 10 ng/ml, at least 15 ng/mL, at least 20 ng/ml, at least 25 ng/ml, at least 30 ng/ml, at least 35 ng/ml, at least 40 ng/ml, at least 45 ng/ml or at least 50 ng/mL.

8. The method of claim 1, wherein the compound, or a pharmaceutically acceptable salt, or solvate thereof, is administered at a daily dose that provides a threshold blood plasma level of at least 10 ng/ml, at least 15 ng/ml, at least 20 ng/ml, at least 25 ng/mL, at least 30 ng/ml, at least 30 ng/ml, at least 35 ng/ml, or at least 50 ng/ml; and a trough blood plasma level greater than 10 ng/ml, 15 ng/mL, or 20 ng/mL.

9. The method of claim 1, wherein the compound, or a pharmaceutically acceptable salt, or solvate thereof, is administered once daily at dose equivalent to an amount of the compound of 10 to 50 mg.

10. The method of claim 1, wherein the compound, or a pharmaceutically acceptable salt, or solvate thereof, is administered at least two times daily, wherein each dose comprises an amount of the compound equivalent to 10 to 30 mg.

11. The method of claim 1, wherein the compound, or a pharmaceutically acceptable salt, or solvate thereof, is administered in the form of an oral solution, oral dispersion, oral suspension or a solid oral dosage form.

12. The method of claim 1, wherein the method further comprises co-administration of at least one additional therapeutic agent.

13. The method of claim 12, wherein the at least one additional therapeutic agent is co-administered concurrently, sequentially, alternatingly or separately.

14. The method of claim 12, wherein the additional therapeutic agent is a CYP3A4 inhibitor, or a pharmaceutically acceptable salt, or solvate thereof.

15. The method of claim 14, wherein the CYP3A4 inhibitor is selected from the group comprising itraconazole, clarithromycin, erythromycin, telithromycin, nefazodone, voriconazole, ketoconazole, atazanavir, darunavir, indinavir, lopinavir, nelfinavir, ritonavir, saquinavir, tipranavir, cobicistat, troleandomycin, telaprevir, danoprevir, elvitegravir, mifepristone, mibefradil, LCL161, posaconazole, grapefruit juice DS, ceritinib, conivaptan, tucatinib, ribociclib, idelalisib and boceprevir, or a pharmaceutically acceptable salt, or solvate thereof.

16. A kit containing: (i) a pharmaceutical unit dosage composition comprising a therapeutically effective amount of the compound of formula (I) or a pharmaceutically acceptable salt, or solvate thereof; and (ii) a pharmaceutical unit dosage composition comprising a therapeutically effective amount of a CYP3A4 CYP34A inhibitor, or a pharmaceutically acceptable salt, or solvate thereof.

17. The kit of claim 16, wherein the CYP3A4 inhibitor is selected from the group comprising itraconazole, clarithromycin, erythromycin, telithromycin, nefazodone, voriconazole, ketoconazole, atazanavir, darunavir, indinavir, lopinavir, nelfinavir, ritonavir, saquinavir, tipranavir, cobicistat, troleandomycin, telaprevir, danoprevir, elvitegravir, mifepristone, mibefradil, LCL161, posaconazole, grapefruit juice DS, ceritinib, conivaptan, tucatinib, ribociclib, idelalisib and boceprevir, erythromycin, fluconazole, atazanavir/ritonavir, darunavir, ACT-539313, duvelisib diltiazem, darunavir/ritonavir, dronedarone, crizotinib, atazanavir, fedratinib, letermovir, GSK2647544, aprepitant, lefamulin, casopitant, amprenavir, faldaprevir, imatinib, verapamil, ravuconazole, netupitant, nilotinib, istradefylline, grapefruit juice tofisopam, cyclosporine, ACT-178882, ciprofloxacin, voxelotor, Magnolia vine (*Schisandra sphenanthera*), isavuconazole, cimetidine,FK1706, fenebrutinib, tabimorelin, amlodipine, rimegepant, ranolazine, breviscapine, lomitapide, fosaprepitant (IV), Seville orange (*Citrus aurantium*) juice, amiodarone, larotrectinib, diosmin, chlorzoxazone, M100240, fluvoxamine, ranitidine, goldenseal, clotrimazole, olaparib, tacrolimus,ASP8477, palbociclib, cilostazol, ticagrelor, peppermint oil, ivacaftor, GSK2248761, Guan Mai Ning, entrectinib, osilodrostat, AZD2327, piperine resveratrol, roxithromycin, suvorexant, propiverine, isoniazid, berberine, hormonal contraceptives, delavirdine, daclatasvir, simeprevir, SCY-078 (MK-3118), atorvastatin, tolvaptan, rucaparib, almorexant, GSK1292263, evacetrapid, linagliptin, grazoprevir (ingredient of Zepatier), lacidipine, cranberry juice, pazopanib, fostamatinib, everolimus, blueberry juice, flibanserin, lapatinib, brodalumab, AMD070, alprazolam, Tong Xin Luo, glecaprevir and pibrentasvir, bicalutamide, sitaxentan, azithromycin, lumateperone, obeticholic acid, ginkgo, teriflunomide, or a pharmaceutically acceptable salt, or solvate thereof.

* * * * *